(12) United States Patent
Shelton, IV et al.

(10) Patent No.: US 10,639,027 B2
(45) Date of Patent: May 5, 2020

(54) SUTURING INSTRUMENT CARTRIDGE WITH TORQUE LIMITING FEATURES

(71) Applicant: Ethicon Endo-Surgery, LLC, Guaynabo, PR (US)

(72) Inventors: Frederick E. Shelton, IV, Hillsboro, OH (US); Daniel J. Mumaw, Liberty Township, OH (US); Emily A. Schellin, Cincinnati, OH (US); Trevor J. Barton, Cincinnati, OH (US); Michael J. Vendely, Lebanon, OH (US); Adam Hensel, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 575 days.

(21) Appl. No.: 14/923,748

(22) Filed: Oct. 27, 2015

(65) Prior Publication Data

US 2017/0112489 A1    Apr. 27, 2017

(51) Int. Cl.
*A61B 17/04* (2006.01)
*A61B 90/00* (2016.01)
*A61B 17/00* (2006.01)

(52) U.S. Cl.
CPC .......... *A61B 17/0469* (2013.01); *A61B 90/03* (2016.02); *A61B 2017/00367* (2013.01); *A61B 2090/031* (2016.02)

(58) Field of Classification Search
CPC .......... A61B 17/0469; A61B 17/07207; A61B 17/0644; A61B 17/1155; A61B 17/34; A61B 17/068; A61B 17/072; A61B 17/105; A61B 17/29; A61B 17/0206; A61B 17/0682; A61B 17/1114; A61B 17/115; A61B 17/1611; A61B 17/1671; A61B 17/32075; A61B 90/03; A61B 90/90; A61B 90/96; A61B 2017/2932; A61B 2017/00004; A61B 2017/00128; A61B 2017/00539; A61B 2017/00831;
(Continued)

(56) References Cited

U.S. PATENT DOCUMENTS

| | | | |
|---|---|---|---|
| 8,702,732 B2 | 4/2014 | Woodard et al. | |
| 8,771,297 B2 * | 7/2014 | Miller .............. | A61B 17/12013 606/113 |
| 9,168,037 B2 | 10/2015 | Woodard et al. | |
| 9,357,998 B2 | 6/2016 | Martin et al. | |
| 9,375,212 B2 | 6/2016 | White et al. | |
| 9,474,522 B2 | 10/2016 | Deck et al. | |
| 2007/0006692 A1 * | 1/2007 | Phan ................. | A61B 17/8875 81/475 |

(Continued)

*Primary Examiner* — Kathleen S Holwerda
*Assistant Examiner* — Brooke Labranche
(74) *Attorney, Agent, or Firm* — Frost Brown Todd LLC

(57) ABSTRACT

A surgical instrument includes a body, a shaft, a cartridge receiving assembly, a suture cartridge, and a slip clutch. The cartridge receiving assembly has a transmission mechanism operatively connected to an actuator of the body. The suture cartridge is received within the cartridge receiving assembly and includes a needle and a drive assembly. The drive assembly is engaged with the transmission mechanism and is coupled with the needle for selectively driving the needle. The slip clutch is operatively connected to the actuator, the transmission mechanism, and the drive assembly such that the slip clutch is configured to transmit a force therethrough from the actuator toward the needle. The slip clutch is configured to slip under the influence of predetermined maximum force transmission therethrough to operatively disengage the needle from the actuator for limiting a driving force applied to the needle.

20 Claims, 14 Drawing Sheets

(58) Field of Classification Search
CPC .. A61B 2017/00862; A61B 2017/0641; A61B 2017/07228; A61B 2017/07264; A61B 2017/0727; A61B 2017/07278; A61B 2017/07285; A61B 2017/2943; A61B 2017/320052; A61B 2017/07257; A61B 2017/00017; A61B 2017/00115; A61B 2017/00022; A61B 2017/00367; A61B 2017/00084; A61B 2017/00119; A61B 2017/00199; A61B 2017/2913; A61B 2017/2919; A61B 2017/292; A61B 2017/2925; A61B 2090/032; A61B 2090/0811; A61B 2090/036; A61B 2090/065; A61B 2090/031; A61B 2090/064; A61B 2090/0801
See application file for complete search history.

(56) References Cited

U.S. PATENT DOCUMENTS

| | | | |
|---|---|---|---|
| 2007/0260257 A1* | 11/2007 | Phan | A61B 17/1617 606/84 |
| 2010/0152751 A1* | 6/2010 | Meade | A61B 17/0469 606/144 |
| 2012/0277768 A1* | 11/2012 | Viola | A61B 17/0469 606/145 |
| 2015/0032133 A1* | 1/2015 | Ferlin | A61B 17/11 606/150 |
| 2015/0351746 A1 | 12/2015 | Martin et al. | |
| 2016/0015380 A1* | 1/2016 | Sholev | A61B 17/0482 606/80 |
| 2016/0367239 A1 | 12/2016 | Mumaw et al. | |
| 2016/0367243 A1 | 12/2016 | Martin et al. | |

* cited by examiner

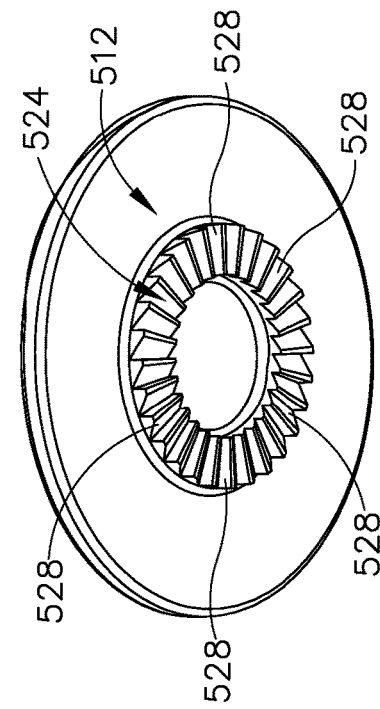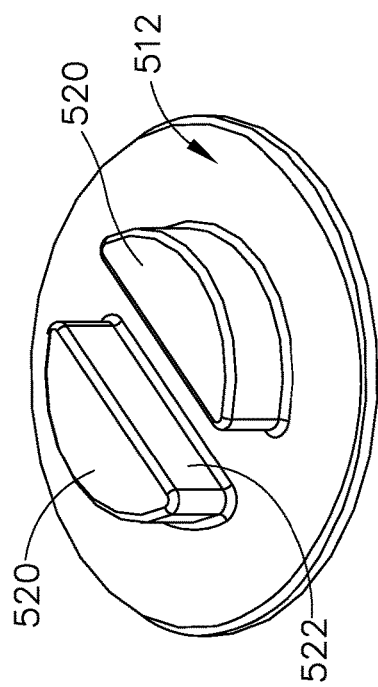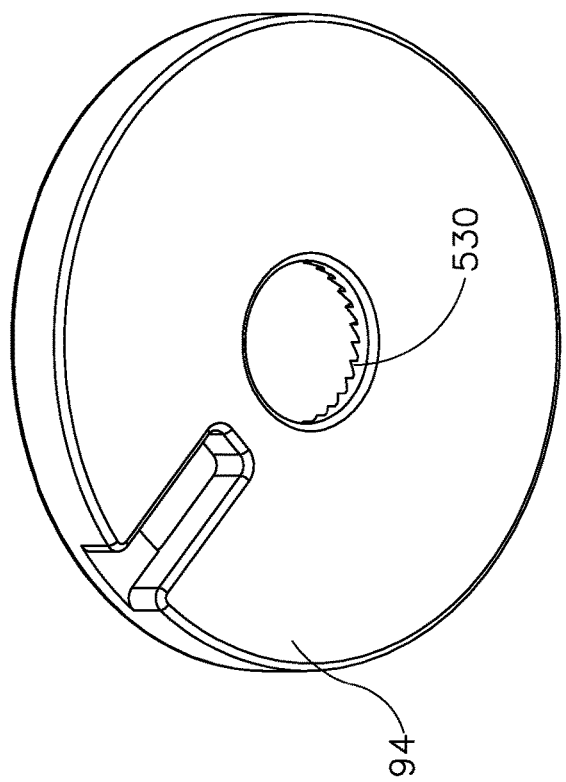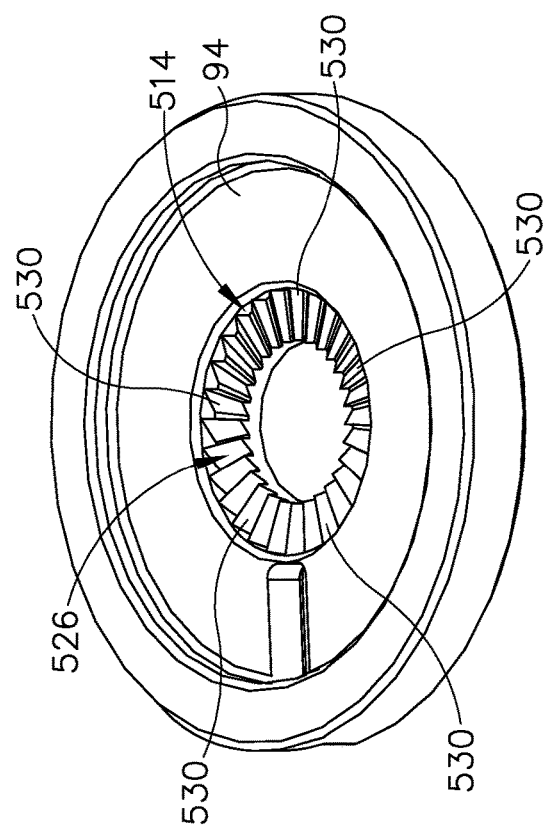

SUTURING INSTRUMENT CARTRIDGE WITH TORQUE LIMITING FEATURES

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pub. No. 2011/0313433, entitled "Laproscopic Suture Device with Asynchronous In-Line Needle Movement," published Dec. 22, 2011, issued as U.S. Pat. No. 9,168,037 on Oct. 27, 2015, the disclosure of which is incorporated by reference herein; U.S. Pub. No. 2014/0171970, entitled "Circular Needle Applier with Articulating and Rotating Shaft," published Jun. 19, 2014, issued as U.S. Pat. No. 9,357,998 on Jun. 7, 2016, the disclosure of which is incorporated by reference herein; and U.S. patent application Ser. No. 14/297,993, entitled "Jawed Receiver for Needle Cartridge," filed Jun. 6, 2014, issued as U.S. Pat. No. 9,474,522 on Oct. 25, 2016, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 18 depicts a bottom perspective view of a rotary input of the cartridge of FIG. 14;

FIG. 19 depicts a top perspective view of the rotary input of FIG. 18;

FIG. 20 depicts a bottom perspective view of a clutch plate of the cartridge of FIG. 14;

FIG. 21 depicts a top perspective view of the clutch plate of FIG. 20;

Figure 1:
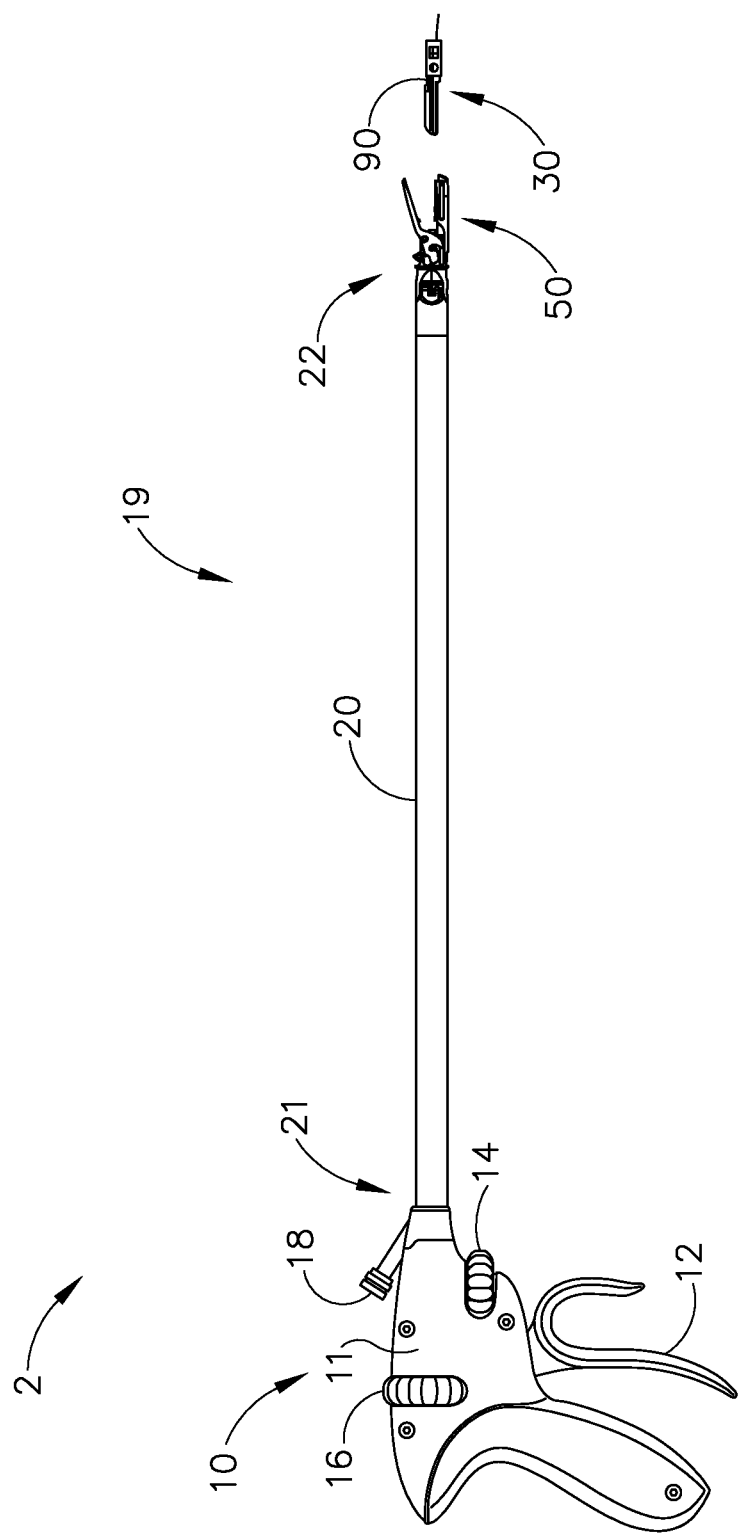
FIG. 1 depicts a side view of a first exemplary surgical suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal", "distal", "upper", and "lower" are defined herein relative to an operator or other operator grasping a surgical instrument having a distal surgical end effector. The term "proximal" refers the position of an element closer to the operator or other operator, and the term "distal" refers to the position of an element closer to the surgical end effector of the surgical instrument and further away from the operator or other operator. The term "upper" refers to the position of the element closer to a top of the surgical instrument when viewed by the operator from above, and the term "lower" refers to the position of the element closer to a bottom of the surgical instrument when viewed by the operator from below. As such, proximal and distal portions are generally in longitudinal opposition as described herein, whereas upper and lower portions are generally in transverse opposition as described herein. In addition, the terms "clockwise," "counterclockwise," "left," and "right" are used below with reference to views as illustrated for clarity and are not intended to limit the invention described herein.

I. OVERVIEW OF EXEMPLARY SURGICAL SUTURING INSTRUMENT

FIG. 1 illustrates an example of a surgical suturing instrument (2). Instrument (2) comprises a handle assembly (10) and a shaft assembly (19) having an elongate shaft (20) extending from a distal end portion (21) to a proximal end portion (22) thereof. Distal end portion (21) includes a cartridge receiving assembly (50), which is operable to receive a needle applier cartridge (30). Shaft (20) defines a longitudinal axis extending from proximal end portion (22) to distal end portion (21). Handle assembly (10) is connected to proximal end portion (21) of shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to distal end portion (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first user input member (12), shown here as a trigger that pivots between opened and closed positions, may be used to selectively actuate needle applier cartridge (30). The trigger may be spring biased to return the trigger to its open position. A second user input member (14), shown here as a rotary knob, may be used to selectively articulate shaft (20). A third user input member (16), shown here as a rotary knob, may be used to selectively rotate needle applier cartridge (30) about shaft (20). Of course, the number, type, configuration, and operation of input members (12, 14, 16) may vary.

Shaft (20) includes an articulation joint (23). Rotary knob (14) is operable to selectively articulate joint (23) via a joint drive assembly (118). Rotary knob (14) rotates in a plane spaced below and generally parallel with shaft (20). An axle (121) connects rotary knob (14) to a disk (not shown) in housing (11) that also rotates in a plane generally parallel with the shaft (20) for position distal end portion (21) of shaft assembly (19) relative to proximal end portion (22).

Figure 2A:
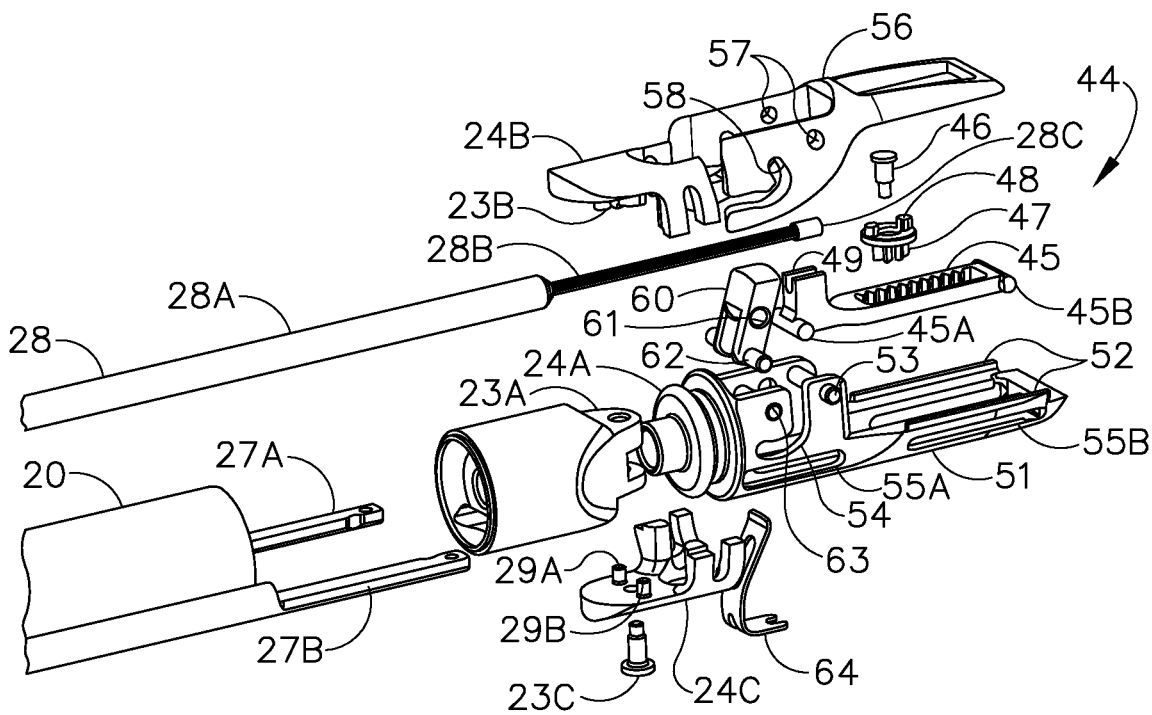
FIG. 2A depicts top perspective exploded view of a cartridge receiving assembly of the instrument of FIG. 1.
Figure 2B:
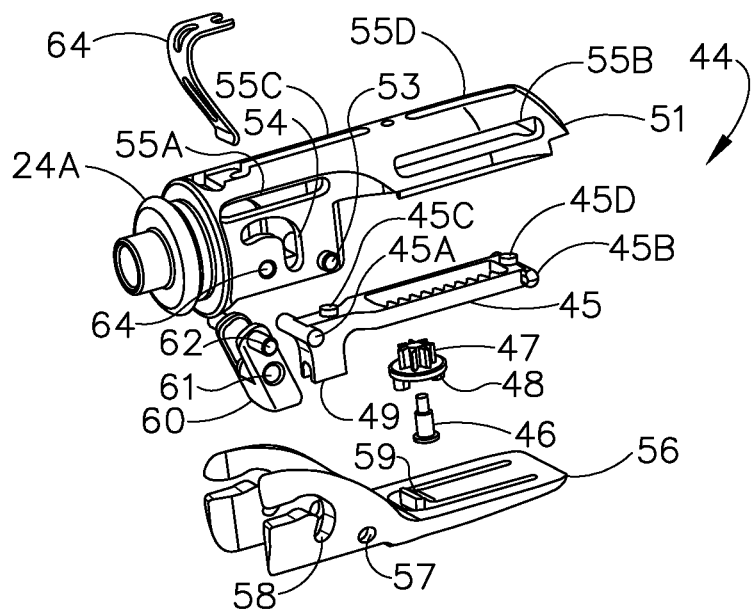
FIG. 2B depicts bottom perspective exploded view of the cartridge receiving assembly of FIG. 2A.

FIGS. 2A-2B illustrate exploded views of cartridge receiving assembly (50) of the present example. Distal end portion (22) of shaft (20) comprises articulation joint (23) and a rotational bearing (24). Articulation joint (23) includes a knuckle (23A) that receives pins (23B, 23C), which are connected to bearing supports (24B, 23C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to rotary knob (14) to opposingly push and pull rods (27A, 27B). In other words, rotary knob (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, 29B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Cartridge receiving assembly (50) includes a transmission mechanism (44) configured to transfer force from input trigger (12) to cartridge (30) for actuation thereof. Transmission mechanism (44) includes rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning A pinion (47) is mounted to lower jaw (51) by a pin (46) in the rack (45) such that longitudinal reciprocation of the rack (45) is converted into rotational reciprocation of pinion (47). A key (48) of transmission mechanism (44) communicates the reciprocating rotation to a rotary input (94) in cartridge body (90), which in turn actuates needle applier cartridge (30).

Drive rod (28) is operatively connected to first user input member (12) and to third user input member (16). Actuation of first user input member (12) will impart axial push and pull loads on drive rod (28) to longitudinally reciprocate rack (45) and thereby actuate needle applier cartridge (30). Actuation of third user input member (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the closed configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received in hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3A:
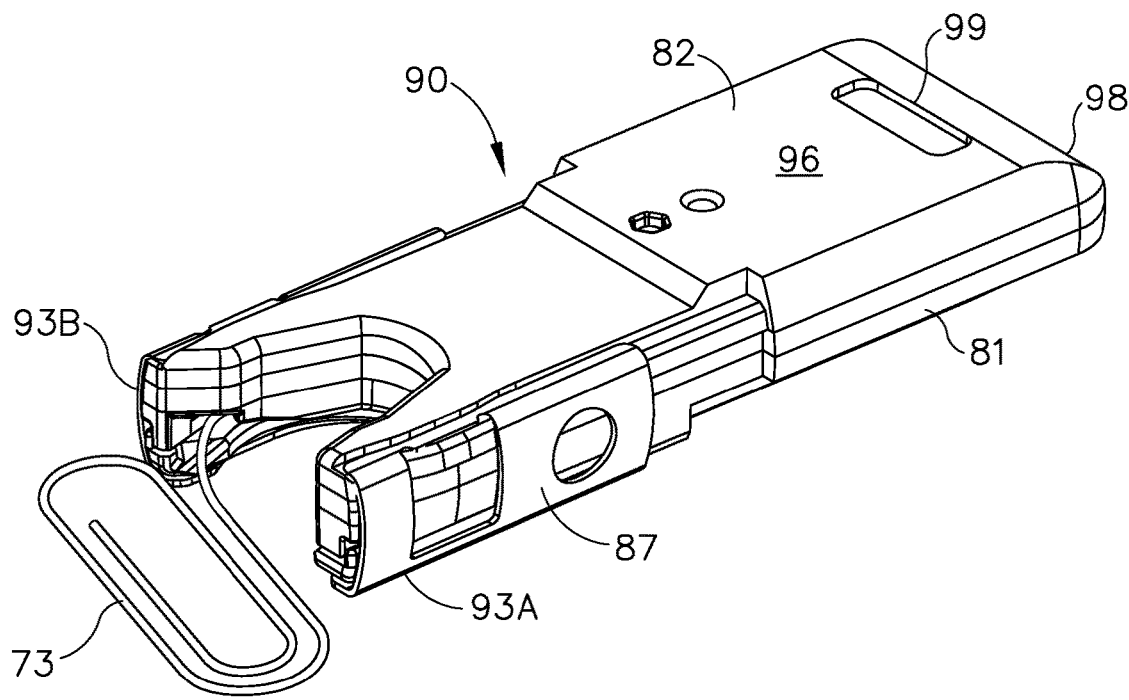
FIG. 3A depicts a top perspective view of a first exemplary cartridge configured for receipt in the cartridge receiving assembly of FIG. 2A.
Figure 3B:
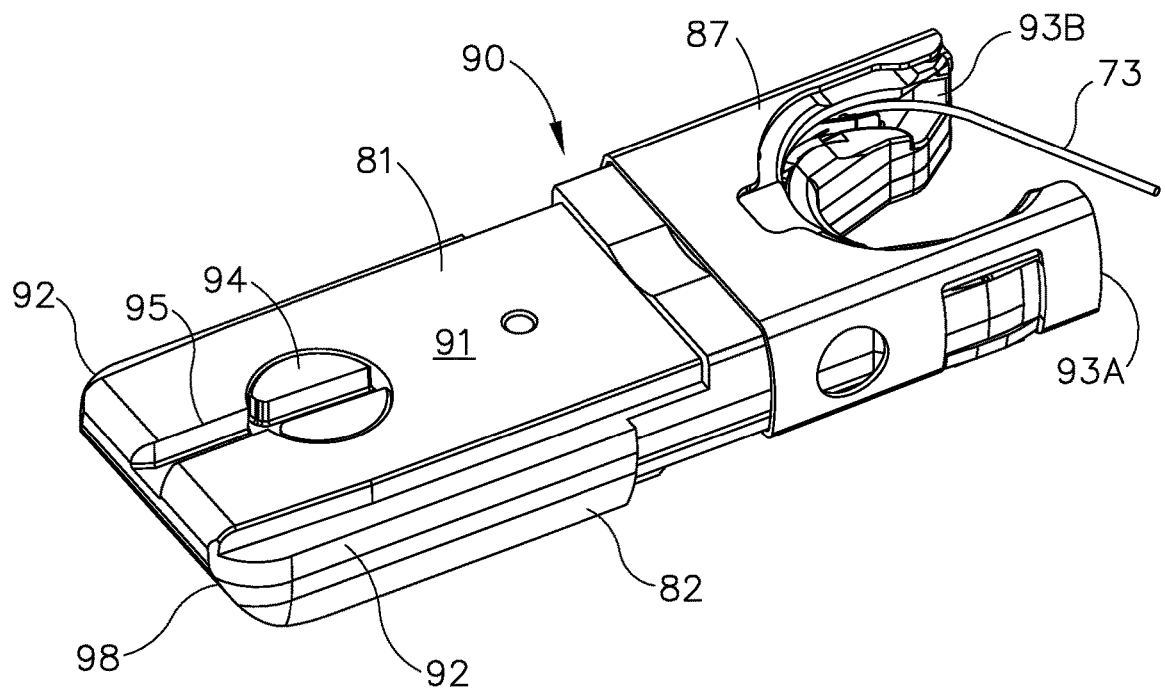
FIG. 3B depicts a bottom perspective view of the cartridge of FIG. 3A.

FIGS. 3A-3B illustrate cartridge body (90) of the present example in greater detail. A lower face (91) of cartridge body (90) is adapted to engage lower jaw (51); and an upper face (96) is adapted to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 4:
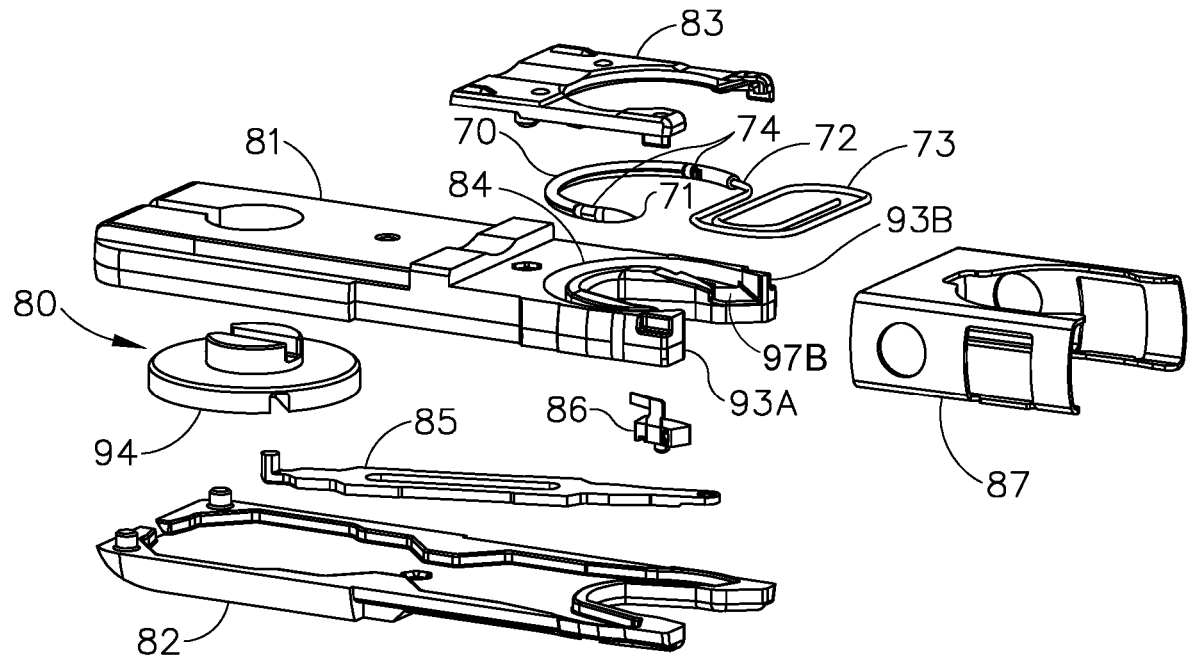
FIG. 4 depicts an exploded view of the cartridge of FIG. 3A.

As shown in FIGS. 3A-4, cartridge body (90) further comprises a lower body (81), an upper body (82), a needle (70), a needle cover (83) and a drive assembly (80) configured to drive needle (70). Drive assembly (80) includes a needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from a trailing end (72) thereof. Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 5A:
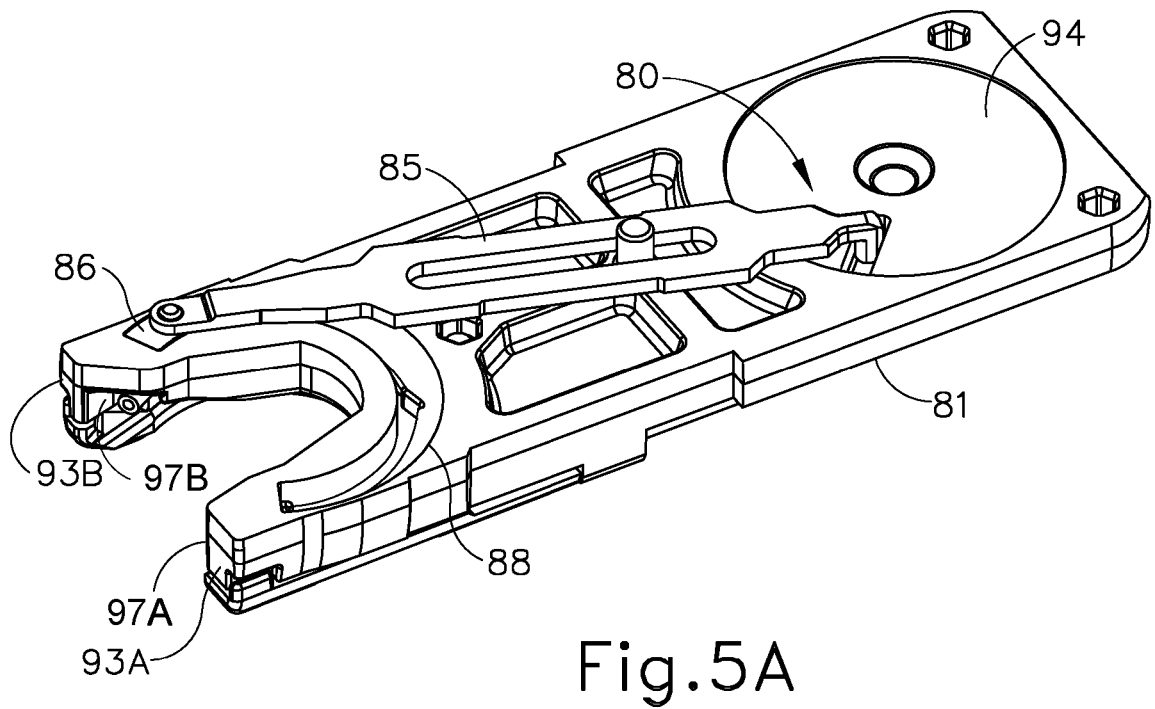
FIG. 5A depicts a perspective view of a drive assembly of the cartridge of FIG. 3A, with the drive assembly at one end of its stroke.
Figure 5B:
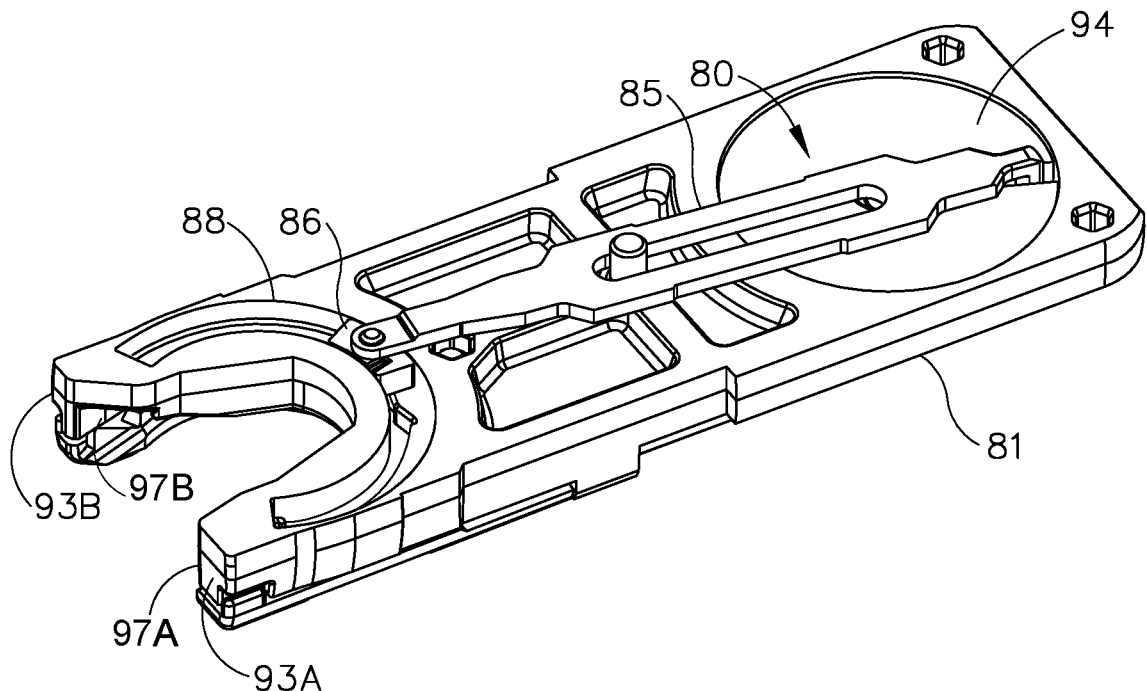
FIG. 5B depicts a perspective view of the drive assembly of FIG. 5A, with the drive assembly at mid-stroke.
Figure 5C:
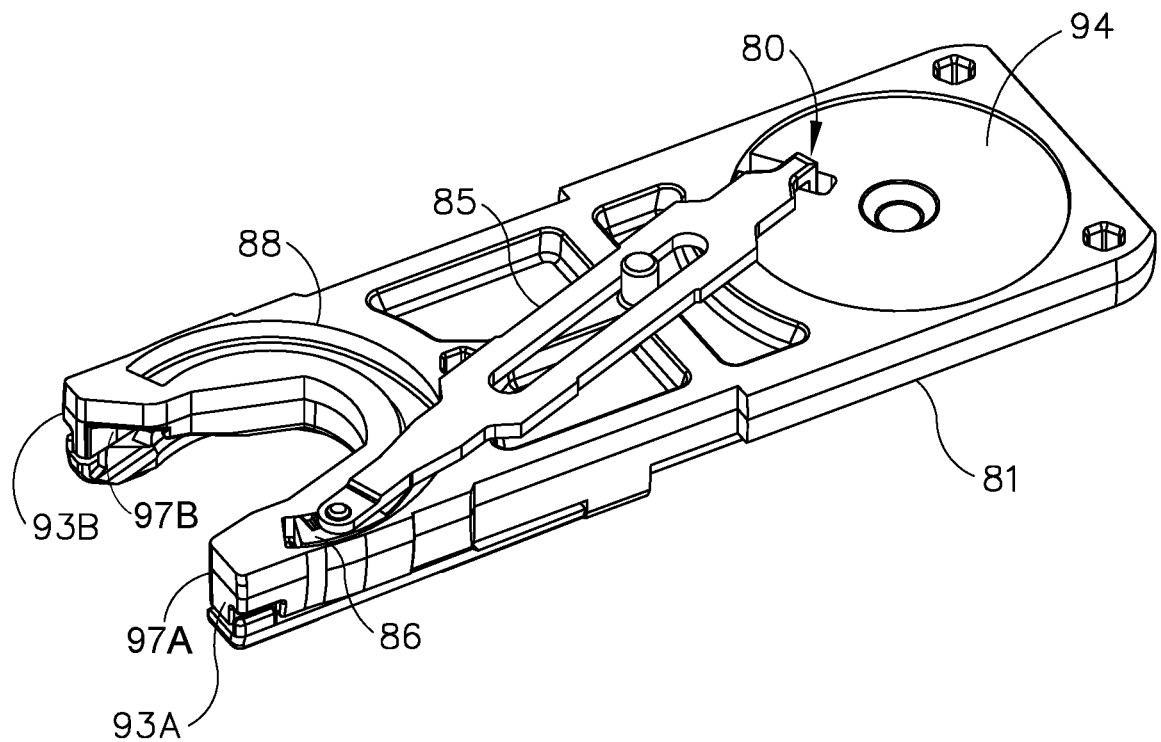
FIG. 5C depicts a perspective view of the drive assembly of FIG. 5A, with the drive assembly at the other end of its stroke.

FIGS. 5A-5C illustrate an example of a drive stroke of the transmission in cartridge body (90) for driving needle (70) in a circular, orbital path. However, it should be understood that needle (70) and suture (73) are omitted from FIGS. 5B-5C for clarity. Needle driver (86) rides in a carrier track

(88) and extends into needle track (84) (see FIG. 4) to engage and drive needle (70). Link (85) connects rotary input (94) to needle driver (86). FIG. 5A shows needle driver (86) positioned at one end of its stroke in carrier track (88). As shown in FIG. 5B, counterclockwise rotation of rotary input (94) will translate needle driver (86) clockwise along carrier track (88), thereby driving needle (70) clockwise. As shown in FIG. 5C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counterclockwise in carrier track (88). Needle driver (86) is disengaged from needle (70) during the return stroke until needle driver (86) reaches the end of the return stroke. Needle driver (86) will re-engage needle (86) upon completing the return stroke. Thus, a sequence of drive and return strokes will rotate the needle (70) in a circular path.

Figure 6:
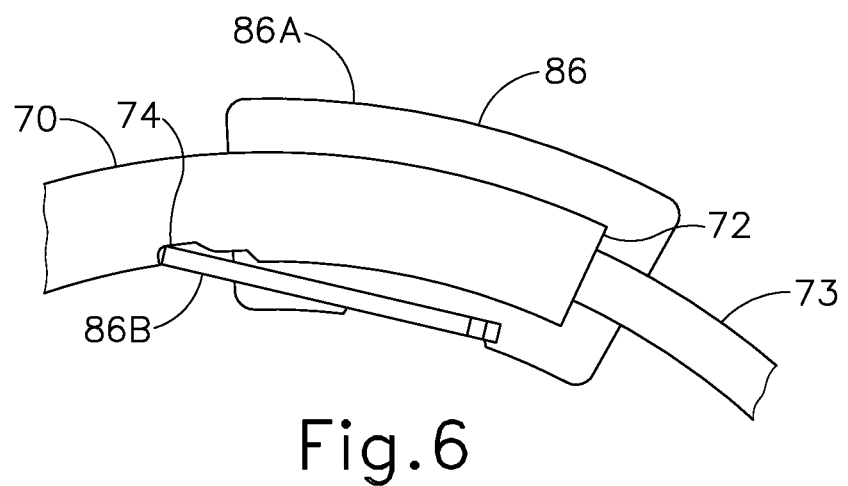
FIG. 6 depicts a partial plan view of a needle driver of the cartridge of FIG. 3A engaging a needle of the cartridge of FIG. 3A.

FIG. 6 illustrates a detailed view of needle driver (86) engaging needle (70). Needle driver (86) comprises a carrier (86A) and a driver (86B). Carrier (86A) is dimensioned to slideably fit in carrier track (88). Driver (86B) is attached to carrier (86A) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 5A-5C and FIG. 6, when first user input member (12) (see FIG. 1) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (97A) and entrance port (97B). Tissue interposed between arms (93A, 93B) will be pierced by leading end (71) of needle (70).

When first user input member (12) (see FIG. 1) is released and the spring return opens the trigger, needle driver (86) reciprocates through its return stroke where it orbits along an angular range of motion about 180 degrees clockwise back to the return position shown in FIG. 5A. During the return stroke, driver (86B) slides over the needle (70). Driver (86B) is then adjacent the distal notch (74). When first user input member (12) is depressed again closing the trigger, needle driver (86) will again be actuated through its drive stroke where it orbits along an angular range of motion about 180 degrees counterclockwise to the driven position as shown in FIG. 5C. During the drive stroke, driver (86B) engages distal notch (74) and will in unison drive needle (70) orbitally along an angular range of motion about 180 degrees back to its retracted position. Suture (73) (see FIG. 3A) will follow needle (70) and be threaded through the pierced tissue.

When first user input member (12) (see FIG. 1) is again released and the spring return opens the trigger, needle driver (86) again reciprocates through its return stroke where it orbits along an angular range of motion about 180 degrees clockwise back to its returned position as shown in FIG. 5A. During the return stroke, driver (86B) slides over needle (70). Thus, needle (70) is driven in a complete circular path spanning an angular range of 360° in response to first user input member (12) being actuated twice. The sequence may be repeated as needed by the surgeon to achieve the desired suturing task.

Further details, explanations, examples, and alternative embodiments of surgical suturing devices and subcomponents of the foregoing are disclosed in U.S. Pub. No. 2014/0171970, entitled "Circular Needle Applier with Articulating and Rotating Shaft," published Jun. 19, 2014, issued as U.S. Pat. No. 9,357,998 on Jun. 7, 2016, the disclosure of which is incorporated by reference herein; U.S. patent application Ser. No. 14/297,993, entitled "Jawed Receiver for Needle Cartridge," filed Jun. 6, 2014, issued as U.S. Pat. No. 9,474,522 on Oct. 25, 2016, the disclosure of which is incorporated by reference herein; U.S. patent application Ser. No. 14/298,038, entitled "Circular Needle Applier with Cleats," filed Jan. 30, 2015, issued as U.S. Pat. No. 9,375,212 on Jun. 28, 2016, the disclosure of which is incorporated by reference herein; and U.S. patent application Ser. No. 14/740,724, entitled "Suturing Instrument with Motorized Needle Drive," filed Jun. 16, 2015, issued as U.S. Pat. No. 9,888,914 on Feb. 13, 2018, the disclosure of which is incorporated by reference herein. It should be understood that such details, explanations, examples, and alternative embodiments may be readily applied to the above-described instrument (10) and subcomponents thereof.

II. EXEMPLARY SUTURE CARTRIDGE HAVING A SLIP CLUTCH

In some instances, it may be desirable to limit a driving force applied to needle (70) while suturing the tissue of the patient. For example, the operator may inadvertently attempt to force needle (70) through a relatively hard object, such as dense tissue or adjacent surgical equipment unintentionally captured between arms (93A, 93B) during the surgical procedure. Attempting to force needle (70) through the relatively hard object will greatly increase the force required to displace needle (70) and, in turn, increase the forces being transmitted through surgical instrument (2). Such forces may increase the likelihood that needle (70), cartridge (30), or another portion of surgical instrument (2) may be damaged during use. The operator may then need to replace cartridge (30), repair surgical instrument (2) or, in the event that the damage to surgical instrument (2) is beyond repair, replace surgical instrument (2) with a new, undamaged surgical instrument (2). Moreover, the increased driving force of needle (70) may also result in damage to surrounding tissue or adjacent surgical equipment.

Damage to surgical equipment and/or tissue may be costly and time consuming to correct, particularly in a fast paced and complex surgical procedure. In some instances, surgical instrument (2), or more particularly cartridge (30), may thus be provided with a slip clutch, such as those discussed below, that limits the driving force applied to needle (70) for inhibiting inadvertent damage to surgical equipment and/or tissue. It may be desirable to provide such a handle assembly, a shaft assembly, and/or a suturing cartridge of surgical instrument (2) so as to provide a disposable/reusable dichotomy. For instance, the replaceable cartridge may be provided as a disposable component while the handle assembly may be sterilized, reprocessed, reused, etc. Various examples of slip clutches will be described in greater detail below; while other examples, such as those having various combinations of features described herein, will be apparent to those of ordinary skill in the art according to the teachings herein. It should be understood that the examples described below may function substantially similar to instrument (2) described above. In particular, the surgical suturing instruments, cartridge receiving assemblies, and cartridges described below may be used to suture tissue. To this end, like numbers referenced below indicate like features discussed above in greater detail.

It should be understood that the force limiting features described below may be used as a substitute or supplement for other force limiting features. By way of example only, the force limiting features described below may be used as a substitute or supplement for the force limiting features described in U.S. patent application Ser. No. 14/298,015, entitled "Force Limited Needle Driver," filed Jun. 6, 2014, issued as U.S. Pat. No. 10,004,490 on Jun. 26, 2018, the disclosure of which is incorporated by reference herein. In addition, it should be understood that the force limiting features described below may be readily incorporated into various kinds of cartridges, such that the teachings herein are not limited to needle applier cartridges (30). By way of example only, the teachings herein may be readily applied to any of the various cartridges described in U.S. patent application Ser. No. 14/740,834, entitled "Suturing Instrument with Multi-Mode Cartridges," filed Jun. 16, 2015, the disclosure of which is incorporated by reference herein.

A. Exemplary Slip Clutch having a Clutch Lever

Figure 7:
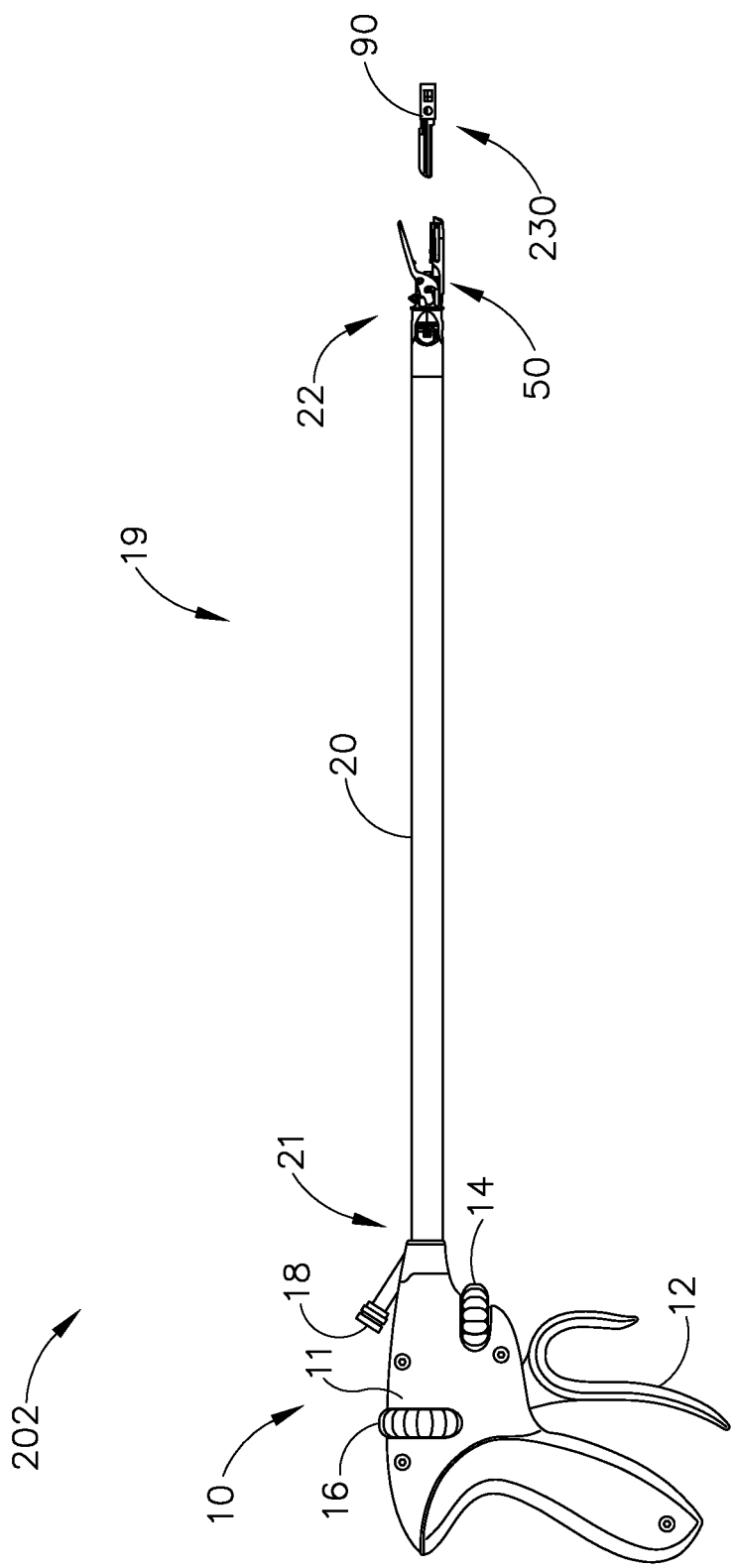
FIG. 7 depicts a side view of a another exemplary surgical suturing instrument.
Figure 8:
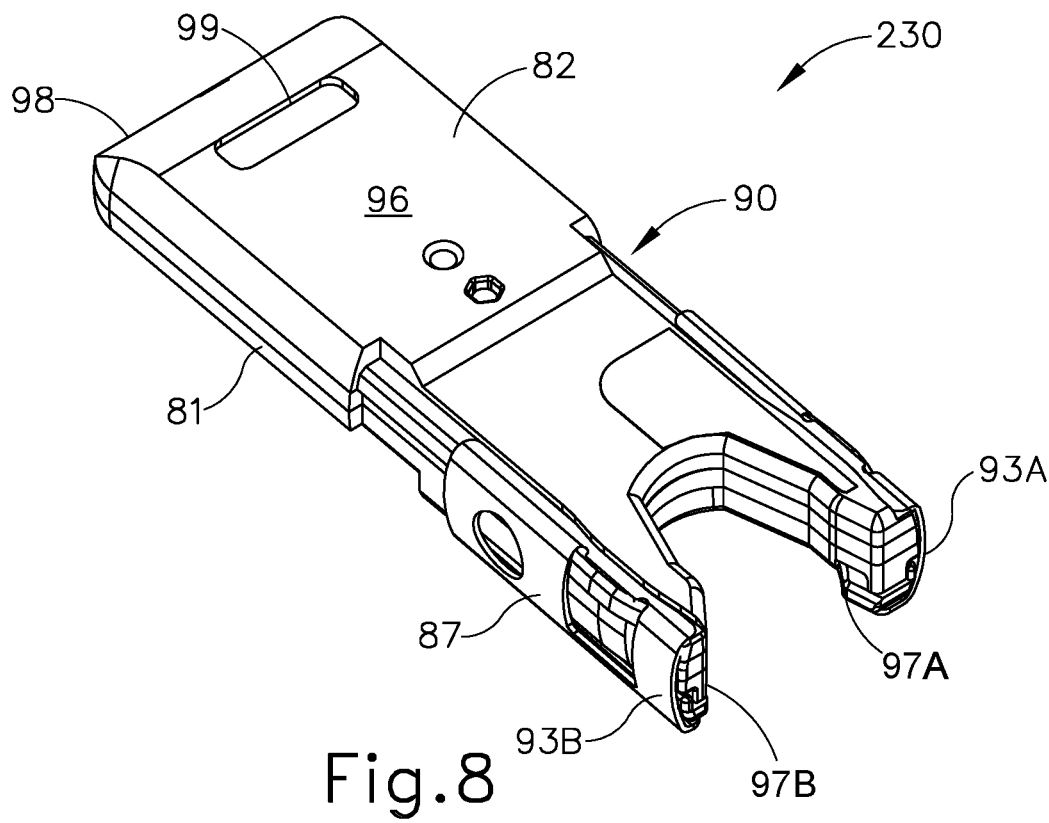
FIG. 8 depicts a top perspective view of an exemplary cartridge configured for use with the instrument of FIG. 7.
Figure 9:
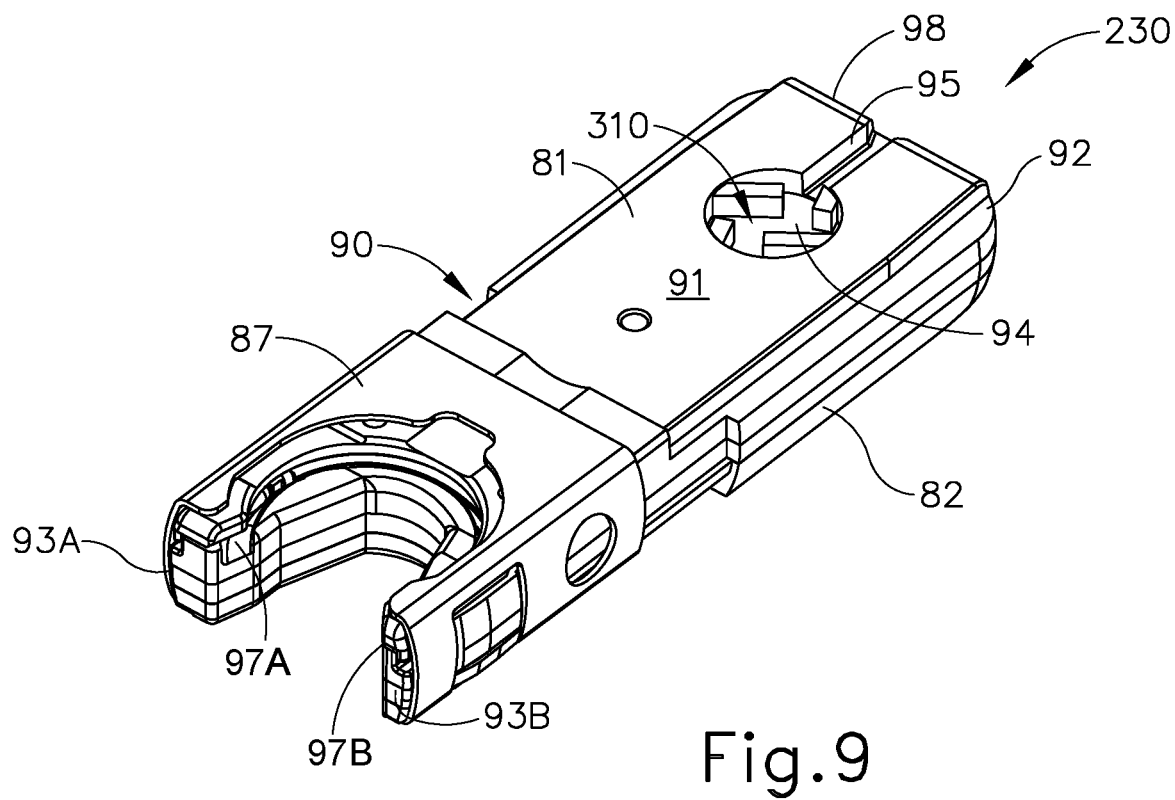
FIG. 9 depicts a bottom perspective view of the cartridge of FIG. 8.

FIGS. 7-9 illustrate a surgical instrument (202) having handle assembly (10), shaft assembly (19), and a needle applier cartridge (230), also referred to herein as a suture cartridge (230). As discussed above with respect to surgical instrument (2) (see FIG. 1), handle assembly (10) includes first user input member (12) in the form of a trigger that may generally be referred to as an actuator. Actuator (12) is configured to be manipulated by the operator for selectively actuating suture cartridge (230) via key (48) of transmission mechanism (44). Suture cartridge (230) includes drive assembly (80) for driving needle (70) along a predetermined orbital path as discussed above. However, in addition, suture cartridge (230) includes a slip clutch (310) that is connected to rotary input (94) and that is configured to releasably connect with key (48) such that suture cartridge (230) may be simply received by and removed from lower jaw (51).

Slip clutch (310) is configured to slip under the influence of a predetermined maximum force transmission therethrough to effectively disengage key (48) from rotary input (94) and allow relative slip therebetween. More particularly, in various examples having rotatable transmission of force from actuator (12) to needle (70), the predetermined maximum force is a predetermined maximum torque. In any case, slip clutch (310) operatively disengages actuator (12) from needle (70) for limiting the drive force applied to needle (70) by operator manipulation of actuator (12). Slip clutch (310) may then operatively reengage actuator (12) to needle (70) in the event that the torque being transmitted to slip clutch (310) decreases to or below the predetermined maximum torque.

Figure 10:
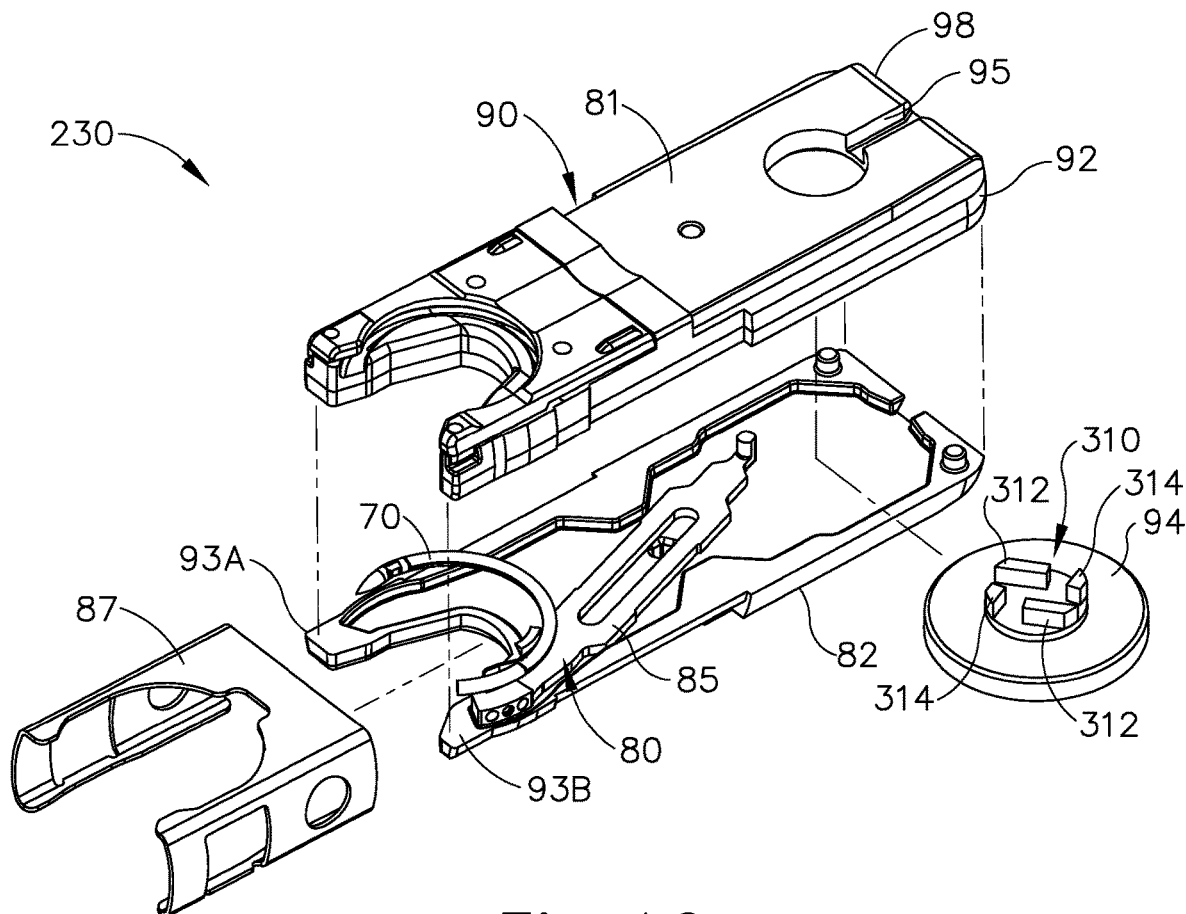
FIG. 10 depicts a partially exploded perspective view of the cartridge of FIG. 8.
Figure 11:
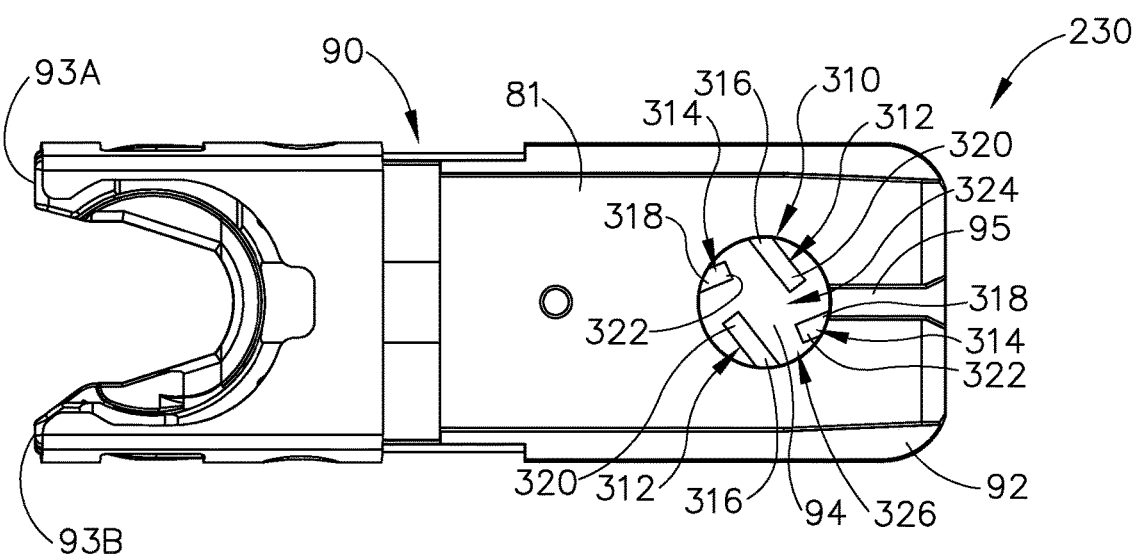
FIG. 11 depicts a bottom plan view of the cartridge of FIG. 8.

FIGS. 9-11 show slip clutch (310) in greater detail having a pair of elongated levers (312) that are offset from each other; and a pair of shortened levers (314) that are also offset from each other and between the pair of elongated levers (312). Outer end portions (316, 318) of elongated and shortened levers (312, 314) are rigidly connected to rotary input (94) and extend downwardly through lower body (81) from rotary input (94). Inner end portions (320, 322) of elongated and shortened levers (312, 314) extend from outer end portions (316, 318) inwardly toward an adjacent outer end portion (318, 316) in a clockwise direction as viewed from below in FIGS. 10-11. Inner end portions (320, 322) thus collectively define a pair of slots (324, 326) that are configured to receive key (48) when received in lower jaw (51) (see FIG. 7).

Inner end portions (320, 322) respectively cantilever from outer end portions (316, 318) such that inner end portions (320, 322) are not rigidly connected to rotary input (94). In various examples, inner end portions (320, 322) are spaced apart from rotary input (94) Inner end portions (320, 322) are resiliently biased relative to outer end portions (316, 318) and are configured to resiliently deform in the clockwise direction under the influence of the predetermined maximum torque. In various alternative examples, inner end portions (320, 322) may be connected to rotary input (94) and may be configured to resiliently deform in the clockwise direction under the influence of the predetermined maximum torque.

Figure 12:
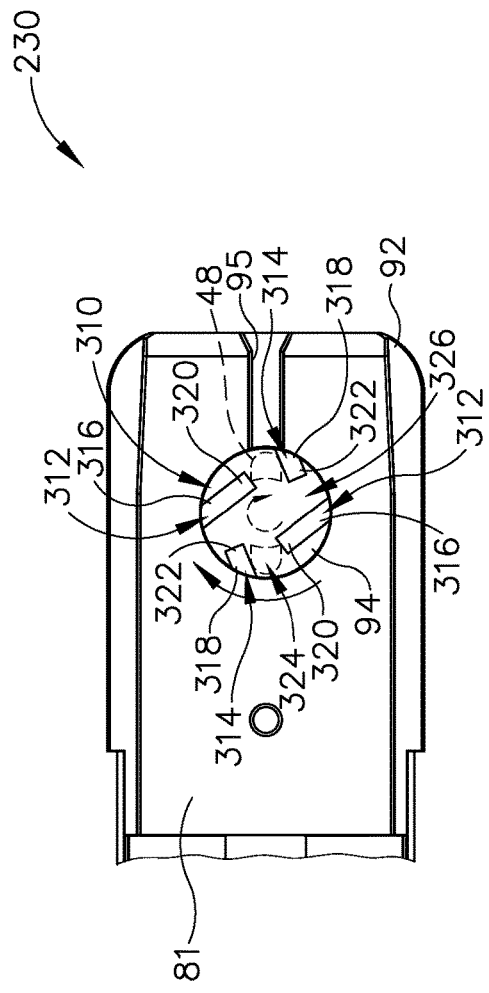
FIG. 12 depicts an enlarged bottom plan view of the cartridge of FIG. 8, with a portion of the instrument of FIG. 7 engaged therewith for clockwise and counterclockwise rotation.
Figure 13B:
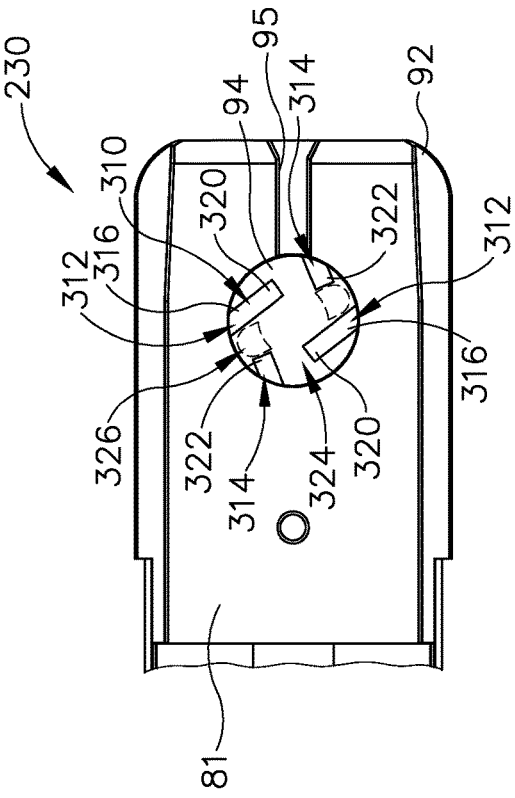
FIG. 13B depicts an enlarged bottom plan view of the cartridge of FIG. 8, with a portion of the instrument of FIG. 7 engaged therewith, and with the rotary input after deflection by the surgical instrument.
Figure 13A:
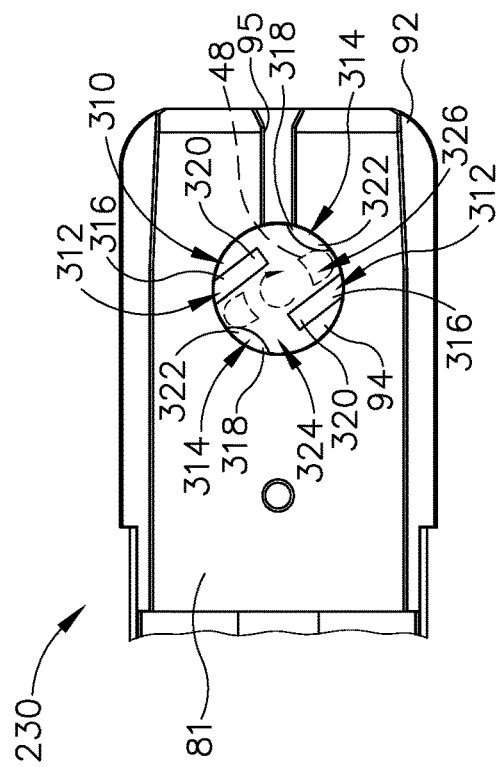
FIG. 13A depicts an enlarged bottom plan view of the cartridge of FIG. 8, with a portion of the instrument of FIG. 7 engaged therewith, and with a rotary input of the cartridge defecting upon clockwise rotation via the surgical instrument.

FIG. 12 shows key (48) received in slot (324). Generally, applying clockwise torque to elongated and shortened levers (312, 314) via key (48) drives slip clutch (310) to rotate and, in turn, rotates rotary input (94) for actuating drive assembly (80) and driving needle (70) in a forward orbital direction as shown in FIG. 12. However, in the event that the clockwise torque applied by key (48) increases beyond the predetermined maximum torque, shortened levers (314) bend clockwise from a first position to a second position, as shown in FIG. 13A, allowing key (48) to slip thereby to slot (326), as shown in FIG. 13B. Elongated levers (312) may than bend clockwise from a first position to a second position to allow key (48) to slip again to slot (324) if the applied torque remains above the predetermined maximum torque. Slip clutch (310) will continue to slip and allow relative rotation between key (48) and rotary input (94) until the applied torque decreases to or below the predetermined maximum torque so as to inhibit damaging surgical instrument (202) (see FIG. 7). In addition, as elongated and shortened levers (312, 314) resiliently bend back and forth to provide for slip, elongated and shortened levers (312) will also generate noise and tactile feedback vibrating back along transmission mechanism (44) causing slight vibrations within actuator (12) (see FIG. 7). The operator may hear the noise and feel the tactile feedback as an indication that the motion of needle (70) is obstructed and may take an appropriate action in response to this obstruction.

As discussed above, elongated and shortened levers (312, 314) are angled relative to each other to allow key (48) to slip by as key (48) rotates in the clockwise direction. This clockwise direction is associated with needle (70) being driven forwardly along the orbital path as described above. In various examples, elongated and shortened levers (312, 314) are also angled relative to each other to prevent key (48) from slipping when rotated in the counterclockwise direction. Key (48) more particularly engages inner end portions (320, 322) of elongated and shortened levers (312, 314) in the counterclockwise direction such that inner end portions (320, 322) are being forced directly back toward outer end portions (316, 318), which rigidly connect to rotary input (94). Elongated and shortened levers (312, 314) are thus unable to deflect and remain engaged with key (48) to prevent counterclockwise slippage of key (48) relative to rotary input (94). Slip clutch (310) will this remain engaged between rotary input (94) and key (48) in the counterclockwise direction.

While slip clutch (310) is shown and described as part of suture cartridge (230) and is configured to be connected between drive assembly (80) of suture cartridge (230) and key (48) of transmission mechanism (44), slip clutch (310) may be alternatively positioned between actuator (12) and needle (70). For example, slip clutch (310) may be directly connected to actuator (12) or needle (70) or included within any one of actuator (12), transmission mechanism (44), or drive assembly (80), so long as slip clutch (310) is operatively connected somewhere between actuator (12) and needle (70) for generating a relative slip for limiting torque being transferred to needle (70). It should therefore be understood that alternative slip clutches in accordance with the invention described herein are not intended to be unnecessarily limited to being positioned within suture cartridge (230) between drive assembly (80) and key (48). In addition, while actuator (12) is manually actuated by the operator in the present example, it will be appreciated that slip clutch (310) may be similarly used with an automatic motorized actuator to similarly generate relative slip in response to torque exceeding a threshold.

B. Exemplary Slip Clutch having a Clutch Plate

Figure 14:
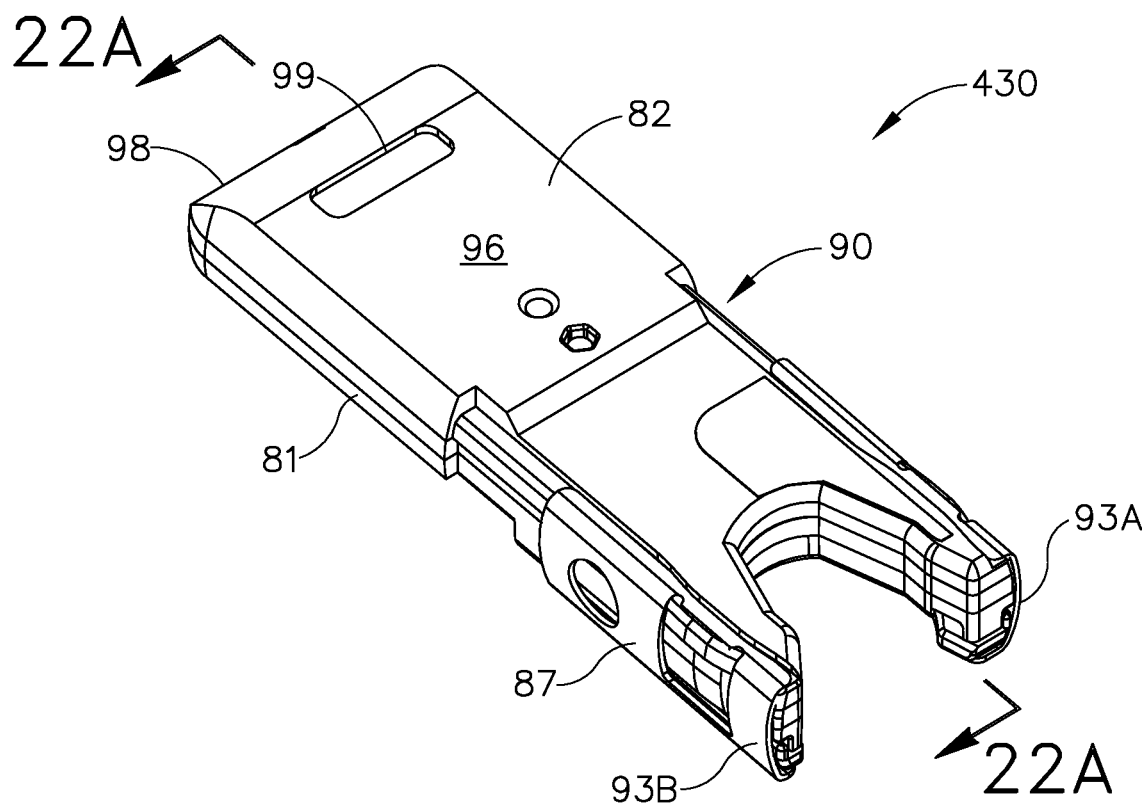
FIG. 14 depicts a top perspective view of another exemplary cartridge configured for use with the instrument of FIG. 7.
Figure 15:
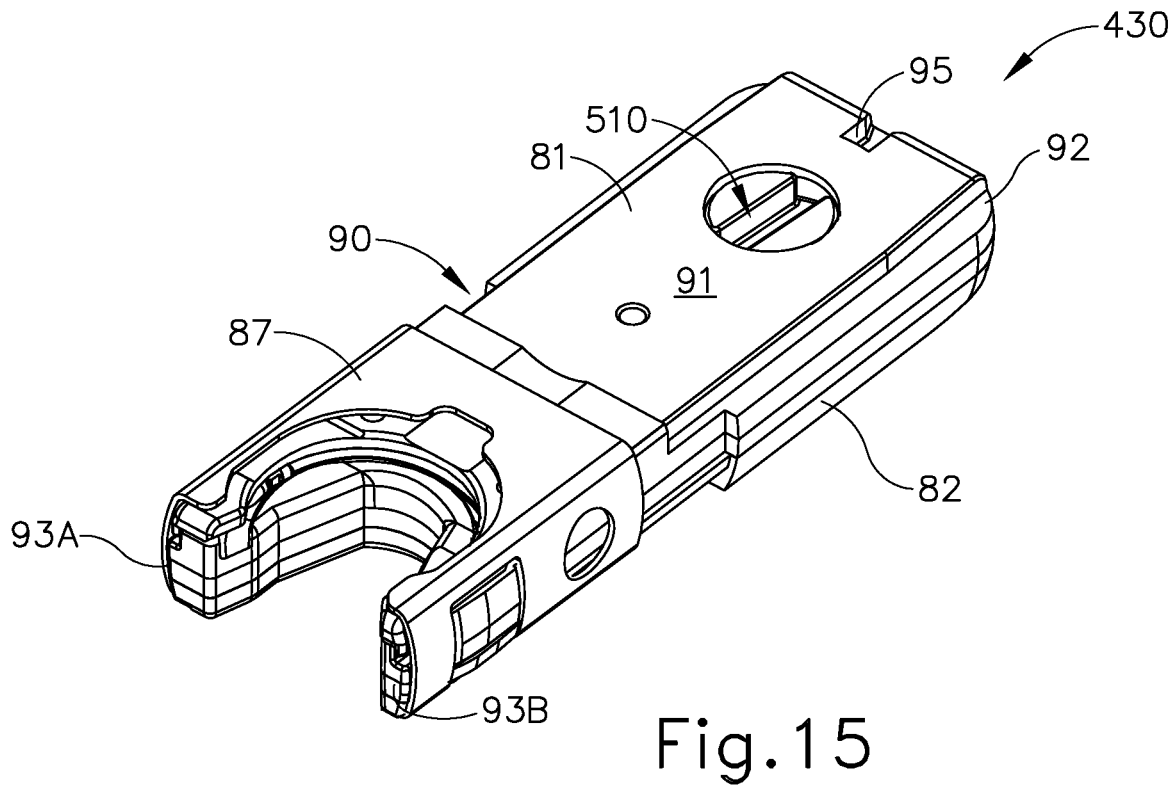
FIG. 15 depicts a bottom perspective view of the cartridge of FIG. 14.
Figure 16:
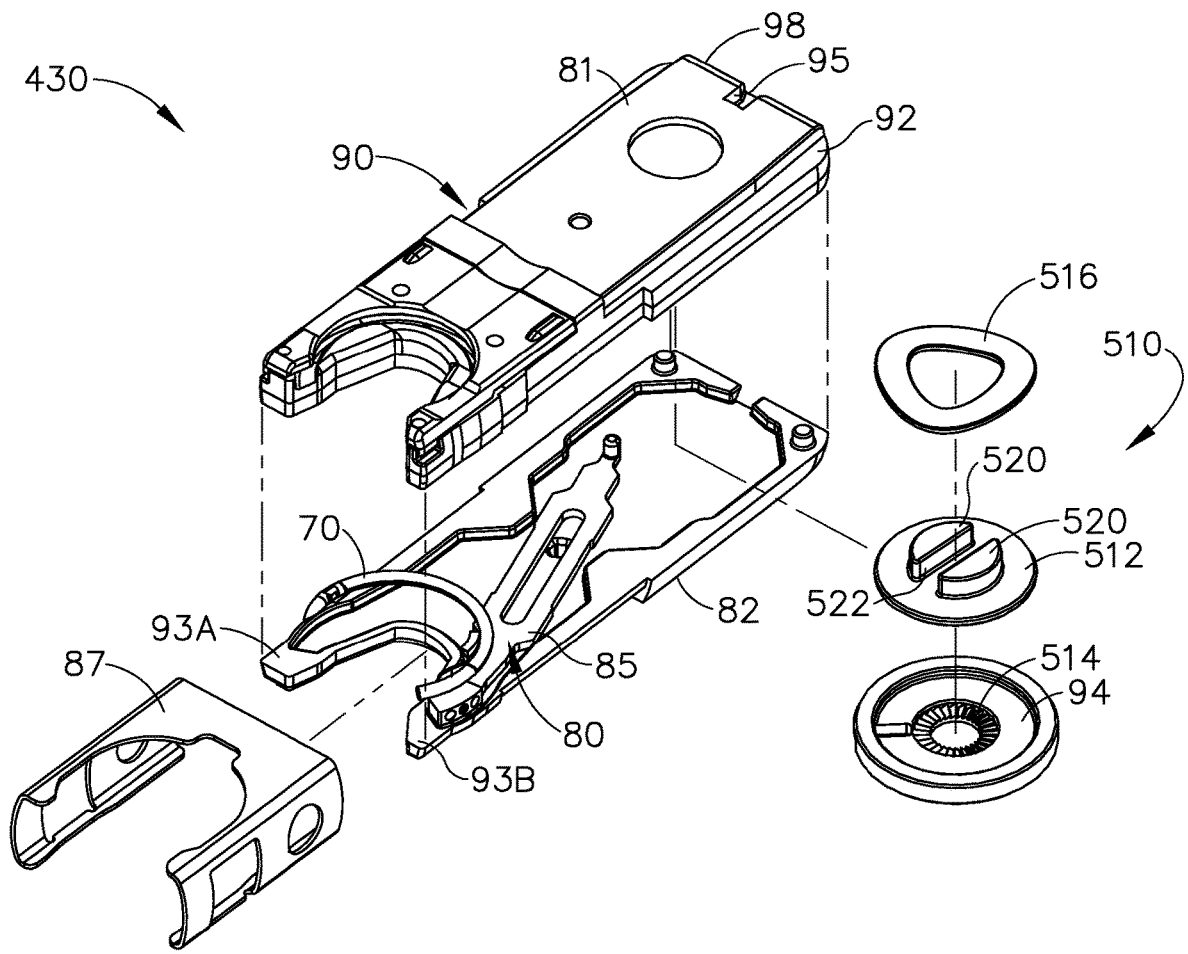
FIG. 16 depicts a partially exploded perspective view of the cartridge of FIG. 14.
Figure 17:
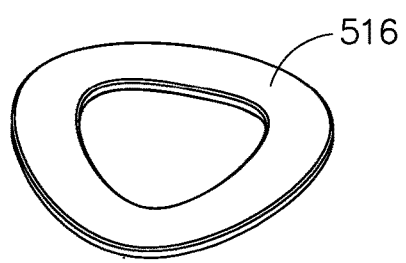
FIG. 17 depicts a bottom perspective view of a wave spring of the cartridge of FIG. 14.

FIGS. 14-16 illustrate another suture cartridge (430) that is configured to be received within lower jaw (51). Suture cartridge (430) includes drive assembly (80) for driving needle (70) along a predetermined orbital path as discussed above. However, in addition, suture cartridge (430) includes a slip clutch (510) that is connected to rotary input (94) and that is configured to releasably connect with key (48) (see FIG. 2A) such that suture cartridge (430) may be simply received by and removed from lower jaw (51). Slip clutch (510) is configured to slip under the influence of a predetermined maximum force transmission therethrough, to effectively disengage key (48) (see FIG. 2A) from rotary input (94) and allow relative slip therebetween. More particularly, in various examples having rotatable transmission of force from actuator (12) to needle (70), the predetermined maximum force is a predetermined maximum torque. In any case, slip clutch (510) operatively disengages actuator (12) from needle (70) for limiting the drive force applied to needle (70) by operator manipulation of actuator (12). Slip clutch (510) may then operatively reengage actuator (12) to needle (70) in the event that the torque being transmitted to slip clutch (510) decreases to or below the predetermined maximum torque.

FIG. 16 shows slip clutch (510) in greater detail having a drive clutch plate (512) releasably engaged with a driven clutch plate (514). Slip clutch (510) further includes a biasing element, such as wave spring (516), configured to bias drive clutch plate (512) in a first position against driven clutch plate (514) for transmitting torque from the drive clutch plate (512) to the driven clutch plate (514). In various examples, driven clutch plate (514) is formed with rotary input (94) as a unitary component such that rotating driven clutch plate (514) similarly rotates rotary input (94) for actuating the drive assembly (80). However, in the event that torque transmitting through drive and driven clutch plates (512, 514) increases beyond the predetermined maximum n, wave spring (516) resiliently deforms, thereby causing the drive plate (514) to translate to the second position and disengage from driven clutch plate (512) and allow relative slip therebetween.

As shown in FIGS. 16-21, wave spring (516) is received between lower body (81) and a lower surface of drive clutch plate (512) in compression to bias drive clutch plate (512) toward driven clutch plate (514) in the first position. Translating drive clutch plate (512) toward the lower body (81) resiliently deflects wave spring (516) in compression until drive clutch plate (512) reaches the second position. The lower surface of drive clutch plate (512) also includes a pair of studs (520) defining a slot (522) therebetween. Regardless of the first or second position, slot (522) is configured to releasably receive key (48) (see FIG. 2A), which is configured to rotate drive clutch plate (512).

To this end, drive clutch plate (512) in the first position is configured to actuate rotary input (94) for driving needle (70) via driven clutch plate (514) therebetween. Drive clutch plate (512) has a drive surface (524), and driven clutch plate (514) has a driven surface (526) that complements drive surface (524). FIGS. 19-20 respectively show drive surface (524) of drive clutch plate (514) and driven surface (526) of driven clutch plate (514) in greater detail. Drive surface (524) has a plurality of drive teeth (528) extending upwardly toward driven clutch plate (514), and driven surface (526) has a plurality of driven teeth (528) extending downwardly toward drive clutch plate (512). In the first position, drive teeth (528) are respectively biased against driven teeth (530) such that drive surface (524) frictionally engages with driven surface (526) for transmitting torque therethrough. The drive teeth (528) and driven teeth (530) are also angled relative to each other (e.g., in sawtooth configurations) to frictionally engage each other at a slip angle between 0 degree and 90 degrees from the plane in which slip clutch (510) is configured to rotate. For example, drive and driven teeth (528, 530) shown in FIGS. 19-20 have a slip angle of approximately 45 degrees.

Figure 22A:
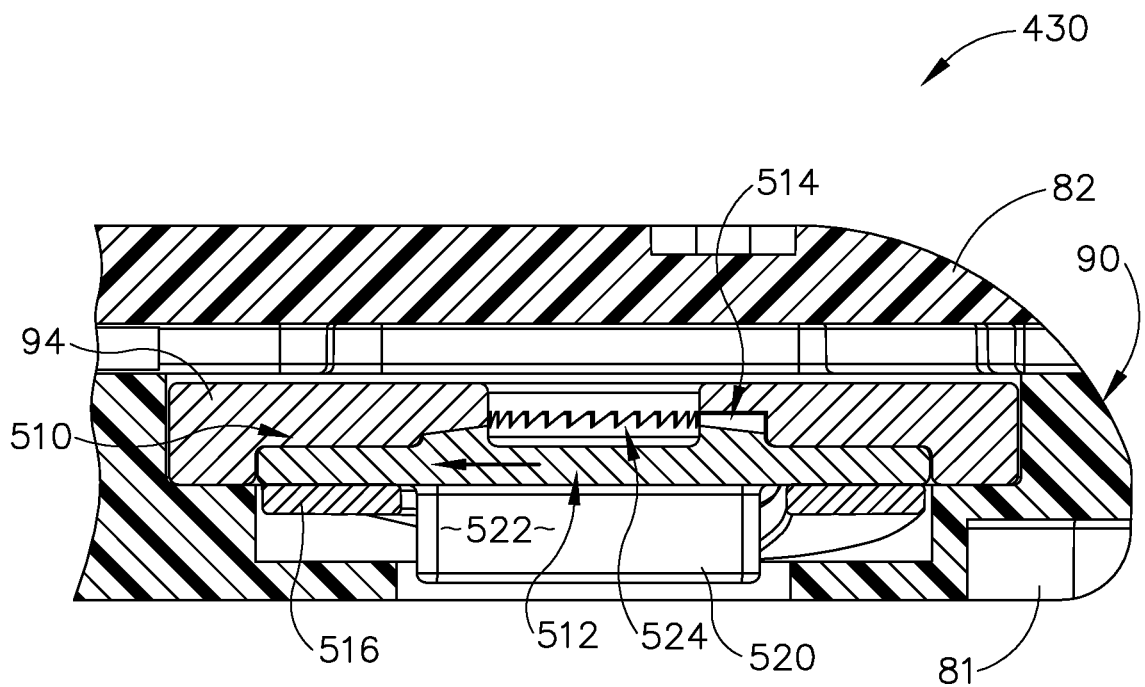
FIG. 22A depicts an enlarged cross-sectional view of the cartridge of FIG. 14, taken along section line 22A-22A of FIG. 14, with the rotary input engaged with the clutch plate.
Figure 22B:
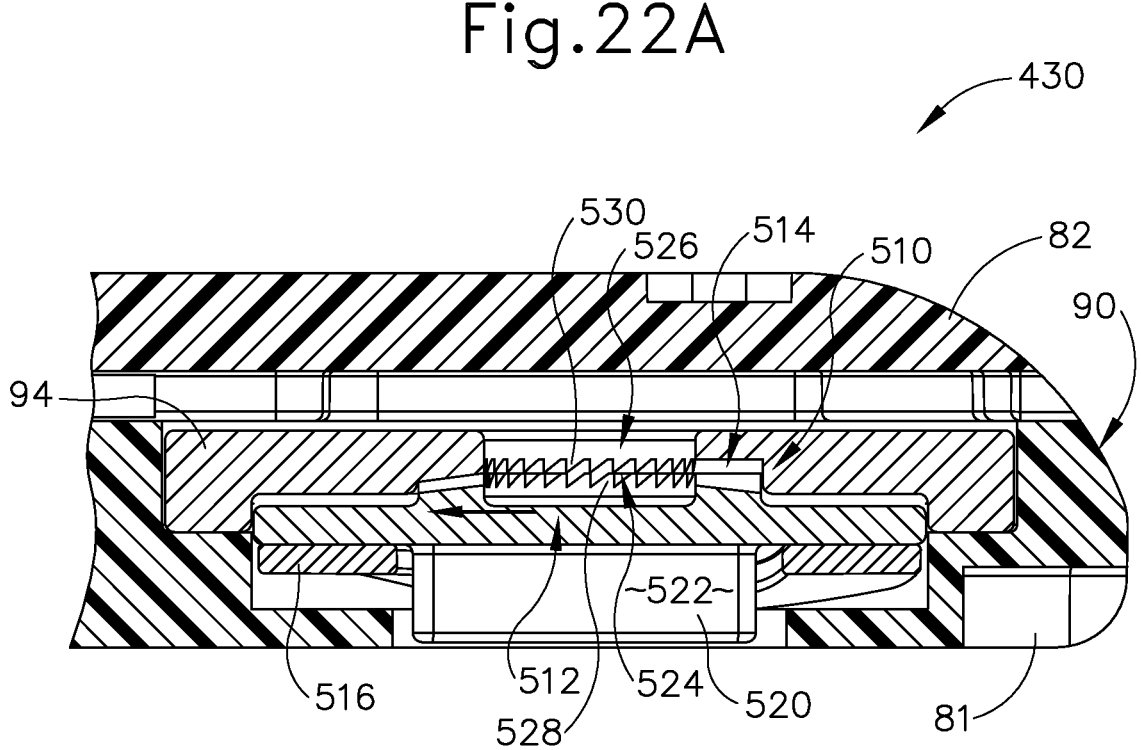
FIG. 22B depicts an enlarged cross-sectional view of the cartridge of FIG. 14, taken along section line 22A-22A of FIG. 14, with the rotary input disengaged from the clutch plate.

In use, rotating drive teeth (528) against driven teeth (530) to the left as shown in FIG. 22A generates a reaction force having vertical and horizontal components in accordance with the slip angle between drive and driven surfaces (524, 526). The horizontal force results in torque being transferred from drive teeth (528) to driven teeth (530). In contrast, the vertical force pushes upwardly against the resiliently mounted drive clutch plate (514), thereby causing the drive clutch plate (514) to move toward the second position and drive teeth (528) to slide up driven teeth (530) as shown in FIG. 22B. As the torque being transferred increases, so too does the vertical force compressing against wave spring (516).

Wave spring (516) is configured to allow drive clutch plate (512) to remain engaged with driven clutch plate (514) until the torque being transferred therethrough increases beyond the predetermined maximum torque. At the predetermined maximum torque, the vertical component of the reaction force overcomes the biasing force of wave spring (516), causing drive clutch plate (514) to slip relative to driven clutch plate (516). Slip clutch (510) will continue to slip and allow relative rotation between key (48) and rotary input (94) until the applied torque decreases to or below the predetermined maximum torque so as to inhibit damaging surgical instrument (202) (see FIG. 7). In addition, as drive teeth (528) slip along driven teeth (530), drive and driven clutch plates (512, 514) will also generate noise and tactile feedback vibrating back along transmission mechanism (44) (see FIG. 16) causing slight vibrations within actuator (12) (see FIG. 7). The operator may hear the noise and feel the tactile feedback as an indication that the motion of needle (70) is obstructed and may take an appropriate action in response to this obstruction.

As discussed above, drive and driven teeth (528, 530) are angled relative to each other to allow drive teeth (528) to slip by driven teeth (530) while being rotatably driven in the left direction shown in FIG. 22A. This left direction is associated with needle (70) being driven forwardly along the orbital path described above. In various examples, drive and driven teeth (528, 530) are also angled relative to each other to prevent key (48) from slipping relative to rotary input (94) if drive teeth (528) are forced to the right relative to driven teeth (530). Drive teeth (528) more particularly engage driven teeth (530) at surfaces being perpendicular to the direction of rotation and, as such, no vertical component of force in generated. Without the vertical component, drive clutch plate (512) remains in the first position and drive teeth (528) similarly remain engaged with driven teeth (530). Slip clutch (510) will this remain engaged between rotary input (94) and key (48) in the right direction.

While slip clutch (510) is shown and described as part of suture cartridge (430) and configured to be connected between drive assembly (80) of suture cartridge (430) and key (48) of transmission mechanism (44), slip clutch (510) may be alternatively positioned between actuator (12) and needle (70) shown in FIG. 7 and FIG. 16. For example, slip clutch (510) may be directly connected to actuator (12) or needle (70) or included within any one of actuator (12), transmission mechanism (44), or drive assembly (80) so long as slip clutch (510) is operatively connected somewhere between actuator (12) and needle (70) for generating a relative slip for limiting torque being transferred to needle (70). It should therefore be understood that alternative slip clutches in accordance with the invention described herein are not intended to be unnecessarily limited to being positioned within suture cartridge (430) between drive assembly (80) and key (48). In addition, while actuator (12) is manually actuated by the operator in the present example, it will be appreciated that slip clutch (510) may be similarly used with an automatic motorized actuator to similarly generate relative slip in response to torque exceeding a threshold.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body having an actuator configured to be selectively manipulated by an operator; (b) a shaft extending distally from the body; (c) a cartridge receiving assembly projecting from a distal end portion of the shaft, wherein the cartridge receiving assembly comprises a transmission mechanism operatively connected to the actuator and configured to be selectively driven via selective manipulation of the actuator; (d) a suture cartridge received within the cartridge receiving assembly, wherein the suture cartridge comprises: (i) a needle, and (ii) a drive assembly engaged with the transmission mechanism and coupled to the needle, wherein the transmission mechanism is configured to actuate the drive assembly and thereby drive the needle along a predetermined path; and (e) a slip clutch operatively connected to the actuator, the transmission mechanism, and the drive assembly such that the actuator is operatively engaged with the needle and configured to transmit a force through the slip clutch for driving the needle, wherein the slip clutch is configured to slip under the influence of a predetermined maximum force transmission therethrough to operatively disengage the needle from the actuator for limiting a driving force applied to the needle.

Example 2

The surgical instrument of Example 1, wherein the slip clutch includes a biased portion configured to resiliently deflect from a first position toward a second position under the influence of the predetermined maximum force, wherein the needle operatively engages the actuator in the first position, and wherein the needle operatively disengages from the actuator in the second position and slips under the influence of the predetermined maximum force.

Example 3

The surgical instrument of Example 2, wherein the biased portion includes a clutch lever configured to resiliently bend from the first position to the second position.

Example 4

The surgical instrument of any one or more of Examples 2 through 3, wherein the biased portion includes a clutch plate, and the clutch plate is resiliently mounted and configured to resiliently translate from the first position to the second position.

Example 5

The surgical instrument of any one or more of Examples 1 through 4, wherein the slip clutch is configured to generate a tactile feedback within the actuator for indicating the slip to an operator.

Example 6

The surgical instrument of any one or more of Examples 1 through 5, wherein the slip clutch is connected between the transmission mechanism of the cartridge receiving assembly and the drive assembly of the suture cartridge.

Example 7

The surgical instrument of Example 6, wherein the predetermined maximum force is a predetermined maximum torque, wherein the transmission mechanism of the cartridge receiving assembly includes a rotatable key output, wherein the drive assembly of the suture cartridge includes a rotary input, wherein the slip clutch is connected between the key output and the rotary input and is configured to slip under the influence of the predetermined maximum torque being transferred therethrough from the key output to the rotary input, wherein the key output is configured to disengage from the rotary input during the slip of the slip clutch for limiting the driving force applied to the needle.

Example 8

The surgical instrument of Example 7, wherein the slip clutch the includes a biased portion configured to resiliently deflect from a first position toward a second position under the influence of the predetermined maximum torque, wherein the key output operatively engages the rotary input in the first position, and wherein the key output operatively disengages from the rotary input in the second position and slips under the influence of the predetermined maximum torque in a forward direction.

Example 9

The surgical instrument of Example 8, wherein the biased portion includes a clutch lever configured to resiliently bend from the first position to the second position, wherein the clutch lever extends from the rotary input toward the key output and is engaged with the key output in the first position, and wherein the clutch lever extends from the rotary input toward the key output and is disengaged from the key output in the second position to slip under the influence of the predetermined maximum torque in the forward direction.

Example 10

The surgical instrument of Example 9, wherein the clutch lever is configured to remain engaged with the key output when directed in a reverse direction opposite the forward direction.

Example 11

The surgical instrument of Example 8, wherein the biased portion includes a clutch plate configured to resiliently translate from the first position to the second position, wherein the clutch plate is resiliently mounted within the suture cartridge and engaged to each of the key output and the rotary input in the first position, and wherein the clutch plate is disengaged from the rotary input in the second position to slip under the influence of the predetermined maximum torque.

Example 12

The surgical instrument of Example 11, wherein the clutch plate has a drive surface, wherein the rotary input has a driven surface, wherein the drive surface is biased against the driven surface such that the drive surface frictionally engages the driven surface in the first position for transmitting torque therethrough.

Example 13

The surgical instrument of Example 12, wherein the drive surface has a plurality of drive teeth, wherein the driven surface has a plurality of driven teeth, wherein the plurality of driven teeth are respectively configured to remain frictionally engaged with the plurality of drive teeth as the clutch plate moves from the first position toward the second position.

Example 14

The surgical instrument of Example 13, wherein the plurality of drive teeth are configured to respectively disengage from the plurality of driven teeth as the clutch plate reaches the second position under the influence of the predetermined maximum torque such that the clutch plate is configured to slip as the key output is rotatably driven a forward direction relative to the rotary input.

Example 15

The surgical instrument of Example 14, wherein the plurality of driven teeth of the rotary input are configured to respectively remain engaged with the plurality of drive teeth when directed in a reverse direction opposite the forward direction.

Example 16

A suture cartridge for a surgical instrument, comprising: (a) a needle; (b) a drive assembly coupled to the needle and having a rotary input, wherein the rotary input is rotatable to actuate the drive assembly and drive the needle along a predetermined path; and (c) a slip clutch connected to the rotary input and configured to transfer a torque for driving the needle, wherein the slip clutch is configured to slip under the influence of a predetermined maximum force transmission therethrough to operatively disengage the needle from the slip clutch for limiting a driving force applied to the needle.

Example 17

The suture cartridge of Example 16, wherein the slip clutch includes a clutch lever configured to resiliently bend from the first position to the second position, wherein the clutch lever extends from the rotary input and is configured to engage with a key output of the surgical instrument in the first position, and wherein the clutch lever extends from the rotary input and is configured to disengage from the key output of the surgical instrument in the second position to slip under the influence of the predetermined maximum torque.

Example 18

The surgical instrument of any one or more of Example 16, wherein the slip clutch includes a clutch plate configured to resiliently translate from the first position to the second position, wherein the clutch plate is resiliently mounted within the suture cartridge and engaged with the rotary input in the first position, and wherein the clutch plate is disengaged from the rotary input in the second position to slip under the influence of the predetermined maximum torque.

Example 19

The surgical instrument of Example 18, wherein the clutch plate has a drive surface, wherein the rotary input has a driven surface, wherein the drive surface is biased against the driven surface such that the drive surface frictionally engages the driven surface in the first position for transmitting torque therethrough.

Example 20

A method of suturing a patient with a surgical instrument, the surgical instrument including a body having an actuator configured to be selectively manipulated by an operator, a shaft extending distally from the body, a cartridge receiving assembly projecting from a distal end portion of the shaft, a suture cartridge, and a slip clutch, wherein the cartridge receiving assembly has a transmission mechanism operatively connected to the actuator is and is configured to be selectively driven via selective manipulation of the actuator, wherein the suture cartridge is received within the cartridge receiving assembly and includes a needle and a drive assembly engaged with the transmission mechanism and coupled to the needle, the transmission mechanism is operable to actuate the drive assembly and thereby drive the needle along a predetermined path, wherein the slip clutch is operatively connected to the actuator, the transmission mechanism, and the drive assembly such that the actuator is operatively engaged with the needle and configured to transmit a torque through the slip clutch for driving the needle, wherein the slip clutch is configured to slip under the influence of a predetermined maximum torque transmission therethrough to operatively disengage the needle from the actuator for limiting a driving force applied to the needle, the method comprising: (a) selectively manipulating the actuator; (b) transmitting a torque through the slip clutch from the actuator and toward the needle; (c) increasing the torque through the slip clutch to the predetermined maximum torque; and (d) slipping the slip clutch to operatively disengage the actuator from the needle and limit the drive force applied to the needle

IV. MISCELLANEOUS

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein, is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body having an actuator configured to be selectively manipulated by an operator;
   (b) a shaft extending distally from the body;
   (c) a cartridge receiving assembly projecting from a distal end portion of the shaft, wherein the cartridge receiving assembly comprises a transmission mechanism operatively connected to the actuator and configured to be selectively driven via selective manipulation of the actuator;
   (d) a suture cartridge received within the cartridge receiving assembly, wherein the suture cartridge comprises:
      (i) a needle track at least partially defining a circular predetermined path, wherein the needle track has an entrance port and an exit port positioned on the circular predetermined path,
      (ii) an arcuate needle positioned within the needle track on the circular predetermined path and configured to be driven along the circular predetermined path in a first circular direction and in an opposite, second circular direction, wherein the arcuate needle is configured to exit the exit port and then enter the entrance port while being driven in the first circular direction, and
      (iii) a drive assembly engaged with the transmission mechanism and coupled to the arcuate needle, wherein the transmission mechanism is configured to actuate the drive assembly and thereby drive the arcuate needle to orbit along the circular predetermined path; and (e) a slip clutch operatively connected to the actuator, the transmission mechanism, and the drive assembly such that the actuator is operatively engaged with the arcuate needle and configured to transmit a force through the slip clutch for driving the arcuate needle in the first or second circular directions, wherein the slip clutch driving the arcuate needle in the first circular direction is configured to slip under the influence of a predetermined maximum force transmission therethrough to operatively disengage the arcuate needle from the actuator for limiting a driving force applied to the arcuate needle, and wherein the slip clutch driving the arcuate needle in the second circular direction is configured to prevent slip under the influence of the predetermined maximum force transmission therethrough such that the arcuate needle remains operatively engaged with the actuator for reversing movement of the arcuate needle.

2. The surgical instrument of claim 1, wherein the slip clutch includes a biased portion configured to resiliently deflect from a first position toward a second position under the influence of the predetermined maximum force, wherein the arcuate needle operatively engages the actuator in the first position, and wherein the arcuate needle operatively disengages from the actuator in the second position and slips under the influence of the predetermined maximum force.

3. The surgical instrument of claim 2, wherein the biased portion includes a clutch lever configured to resiliently and arcuately bend from the first position to the second position.

4. The surgical instrument of claim 2, wherein the biased portion includes a clutch plate, and the clutch plate is resiliently mounted and configured to resiliently translate from the first position to the second position.

5. The surgical instrument of claim 1, wherein the slip clutch is configured to generate a tactile feedback within the actuator for indicating the slip to an operator.

6. The surgical instrument of claim 1, wherein the slip clutch is connected between the transmission mechanism of the cartridge receiving assembly and the drive assembly of the suture cartridge.

7. The surgical instrument of claim 6, wherein the predetermined maximum force is a predetermined maximum torque, wherein the transmission mechanism of the cartridge receiving assembly includes a rotatable key output, wherein the drive assembly of the suture cartridge includes a rotary input, wherein the slip clutch is connected between the key output and the rotary input and is configured to slip under the influence of the predetermined maximum torque being transferred therethrough from the key output to the rotary input, wherein the key output is configured to disengage from the rotary input during the slip of the slip clutch for limiting the driving force applied to the arcuate needle.

8. The surgical instrument of claim 7, wherein the slip clutch includes a biased portion configured to resiliently deflect from a first position toward a second position under the influence of the predetermined maximum torque, wherein the key output operatively engages the rotary input in the first position, and wherein the key output operatively disengages from the rotary input in the second position and slips under the influence of the predetermined maximum torque in a forward direction.

9. The surgical instrument of claim 8, wherein the biased portion includes a clutch lever configured to resiliently and arcuately bend from the first position to the second position, wherein the clutch lever extends from the rotary input toward the key output and is engaged with the key output in the first position, and wherein the clutch lever extends from the rotary input toward the key output and is disengaged from the key output in the second position to slip under the influence of the predetermined maximum torque in the forward direction.

10. The surgical instrument of claim 9, wherein the clutch lever is configured to remain engaged with the key output when directed in a reverse direction opposite the forward direction.

11. The surgical instrument of claim 8, wherein the biased portion includes a clutch plate configured to resiliently translate from the first position to the second position, wherein the clutch plate is resiliently mounted within the suture cartridge and engaged to each of the key output and the rotary input in the first position, and wherein the clutch plate is disengaged from the rotary input in the second position to slip under the influence of the predetermined maximum torque.

12. The surgical instrument of claim 11, wherein the clutch plate has a drive surface, wherein the rotary input has a driven surface, wherein the drive surface is biased against the driven surface such that the drive surface frictionally engages the driven surface in the first position for transmitting torque therethrough.

13. The surgical instrument of claim 12, wherein the drive surface has a plurality of drive teeth, wherein the driven surface has a plurality of driven teeth, wherein the plurality of driven teeth are respectively configured to remain frictionally engaged with the plurality of drive teeth as the clutch plate moves from the first position toward the second position.

14. The surgical instrument of claim 13, wherein the plurality of drive teeth are configured to respectively disengage from the plurality of driven teeth as the clutch plate reaches the second position under the influence of the predetermined maximum torque such that the clutch plate is configured to slip as the key output is rotatably driven a forward direction relative to the rotary input.

15. The surgical instrument of claim 14, wherein the plurality of driven teeth of the rotary input are configured to respectively remain engaged with the plurality of drive teeth when directed in a reverse direction opposite the forward direction.

16. The suture cartridge of claim 1, wherein slip clutch includes a biased portion configured to resiliently and arcuately deflect from a first position toward a second position to thereby slip under the influence of a predetermined maximum force transmission.

17. A suture cartridge for a surgical instrument, comprising:
(a) a needle track at least partially defining a circular predetermined path, wherein the needle track has an entrance port and an exit port positioned on the circular predetermined path;
(b) an arcuate needle positioned within the needle track on the circular predetermined path and configured to be driven along the circular predetermined path in a circular direction, wherein the arcuate needle is configured to exit the exit port and then enter the entrance port while being driven in the circular direction;
(c) a drive assembly coupled to the arcuate needle and having a rotary input, wherein the rotary input is rotatable to actuate the drive assembly and drive the arcuate needle to orbit along the circular predetermined path; and (d) a slip clutch connected to the rotary input and configured to transfer a torque for driving the arcuate needle, wherein the slip clutch includes a biased portion configured to resiliently and arcuately deflect from a first position toward a second position to thereby slip under the influence of a predetermined maximum force transmission therethrough to operatively disengage the arcuate needle from the slip clutch for limiting a driving force applied to the arcuate needle.

18. The suture cartridge of claim 17, wherein the biased portion includes a clutch lever configured to resiliently and arcuately bend from the first position to the second position, wherein the clutch lever extends from the rotary input and is configured to engage with a key output of the surgical instrument in the first position, and wherein the clutch lever extends from the rotary input and is configured to disengage from the key output of the surgical instrument in the second position to slip under the influence of the predetermined maximum torque.

19. The suture cartridge of claim 18, wherein the clutch lever is configured to resiliently and arcuately bend radially outward from the first position to the second position.

20. A suture cartridge for a surgical instrument, comprising: (a) a needle track at least partially defining a circular predetermined path, wherein the needle track has an entrance port and an exit port positioned on the circular predetermined path; (b) an arcuate needle positioned within the needle track on the circular predetermined path and configured to be driven along the circular predetermined path in a first circular direction and in an opposite, second circular direction, wherein the arcuate needle is configured to exit the exit port and then enter the entrance port while being driven in the first circular direction; (c) a drive assembly coupled to the arcuate needle and having a rotary input, wherein the rotary input is rotatable to actuate the drive assembly and drive the arcuate needle to orbit along the circular predetermined path; and (d) a slip clutch connected to the rotary input and configured to transfer a torque for driving the arcuate needle in the first or second circular directions, wherein the slip clutch driving the arcuate needle in the first circular direction is configured to slip under the influence of a predetermined maximum force transmission therethrough to operatively disengage the arcuate needle from the slip clutch for limiting a driving force applied to the arcuate needle, and wherein the slip clutch driving the arcuate needle in the second circular direction is configured to prevent slip under the influence of the predetermined maximum force transmission therethrough such that the arcuate needle remains operatively engaged with the slip clutch for reversing movement of the arcuate needle.

* * * * *